United States Patent
Kim et al.

(10) Patent No.: US 9,224,961 B2
(45) Date of Patent: Dec. 29, 2015

(54) CONDENSED-CYCLIC COMPOUND, ORGANIC LIGHT-EMITTING DIODE COMPRISING THE SAME AND FLAT PANEL DISPLAY DEVICE COMPRISING THE ORGANIC LIGHT-EMITTING DIODE

(75) Inventors: Young-Kook Kim, Yongin (KR); Seok-Hwan Hwang, Yongin (KR); Hye-Jin Jung, Yongin (KR); Jin-O Lim, Yongin (KR); Jong-Hyuk Lee, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 844 days.

(21) Appl. No.: 13/240,894

(22) Filed: Sep. 22, 2011

(65) Prior Publication Data

US 2012/0097932 A1    Apr. 26, 2012

(30) Foreign Application Priority Data

Oct. 25, 2010    (KR) ........................ 10-2010-0104180

(51) Int. Cl.
| | |
|---|---|
| H01L 51/54 | (2006.01) |
| C07D 209/56 | (2006.01) |
| C07D 401/02 | (2006.01) |
| C07D 403/02 | (2006.01) |
| C07D 487/22 | (2006.01) |
| H01L 27/32 | (2006.01) |
| H01L 51/00 | (2006.01) |
| H01L 51/50 | (2006.01) |

(52) U.S. Cl.
CPC .......... *H01L 51/0072* (2013.01); *C07D 209/56* (2013.01); *H01L 51/0052* (2013.01); *H01L 51/0059* (2013.01); *H01L 51/5012* (2013.01); *H01L 51/5048* (2013.01)

(58) Field of Classification Search
CPC .. C09K 11/06; C07D 209/56; H01L 51/0052; H01L 51/0059; H01L 51/0072; H01L 51/5012; H01L 51/5048
See application file for complete search history.

(56) References Cited

U.S. PATENT DOCUMENTS

| 5,972,247 A | 10/1999 | Shi et al. |
|---|---|---|
| 6,465,115 B2 | 10/2002 | Shi et al. |
| 6,596,415 B2 | 7/2003 | Shi et al. |
| 7,550,207 B2 | 6/2009 | Sohn et al. |

(Continued)

FOREIGN PATENT DOCUMENTS

| JP | 08012600 | 1/1996 |
|---|---|---|
| JP | 2000003782 | 1/2000 |

(Continued)

*Primary Examiner* — Dawn L. Garrett
(74) *Attorney, Agent, or Firm* — Robert E. Bushnell, Esq.

(57) ABSTRACT

A condensed-cyclic compound of Formula 1, an organic light-emitting diode (OLED) including the same and a flat panel display device including the OLED. The condensed-cyclic compound of Formula 1 may be used in an organic light-emitting diode. Accordingly, an OLED according to an embodiment of the present invention includes a first electrode, a second electrode disposed opposite to the first electrode, and a first layer interposed between the first electrode and the second electrode, wherein the first layer includes the condensed-cyclic compound represented by Formula 1. The OLED may further include at least one layer selected from the group consisting of a hole injection layer, a hole transport layer, an emission layer, a hole blocking layer, an electron transport layer and an electron injection layer.

21 Claims, 2 Drawing Sheets

(56) References Cited

U.S. PATENT DOCUMENTS

| | | | |
|---|---|---|---|
| 2008/0124455 A1* | 5/2008 | Shin et al. | 427/66 |
| 2008/0220285 A1 | 9/2008 | Vestweber et al. | |
| 2008/0224129 A1* | 9/2008 | Choi et al. | 257/40 |
| 2009/0295276 A1 | 12/2009 | Asari et al. | |
| 2012/0091446 A1* | 4/2012 | Jung et al. | 257/40 |
| 2013/0032787 A1* | 2/2013 | Kim et al. | 257/40 |
| 2013/0053558 A1* | 2/2013 | Pflumm et al. | 544/180 |
| 2013/0113367 A1* | 5/2013 | Jung et al. | 313/504 |

FOREIGN PATENT DOCUMENTS

| | | | |
|---|---|---|---|
| KR | 1020080015865 | | 2/2008 |
| KR | 1020080085000 | | 9/2008 |
| KR | 1020100003624 | | 1/2010 |
| KR | 10-1029082 | * | 4/2011 |
| WO | 2008006449 | | 1/2008 |
| WO | WO 2010/151083 | * | 12/2010 |
| WO | WO 2011/025282 | * | 3/2011 |
| WO | WO 2011/057701 | * | 5/2011 |

* cited by examiner

CONDENSED-CYCLIC COMPOUND, ORGANIC LIGHT-EMITTING DIODE COMPRISING THE SAME AND FLAT PANEL DISPLAY DEVICE COMPRISING THE ORGANIC LIGHT-EMITTING DIODE

CLAIM PRIORITY

This application claims the benefit of Korean Patent Application No. 10-2010-0104180, filed on Oct. 25, 2010, in the Korean Intellectual Property Office, the disclosure of which is incorporated herein in its entirety by reference.

BACKGROUND OF THE INVENTION

1. Field of the Invention

The present invention relates to a condensed-cyclic compound, an organic light-emitting diode (OLED) including the same and a flat panel display device including the organic light-emitting diode.

2. Description of the Related Art

Organic light-emitting diodes, which are self-emitting devices, have advantages such as a wide viewing angle, excellent contrast, quick response, high brightness, and excellent driving voltage characteristics, and can provide multicolored images.

A general OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF THE INVENTION

The present invention provides a condensed-cyclic compound, an organic light-emitting diode (OLED) including the same and a flat panel display device including the organic light-emitting diode.

According to an aspect of the present invention, there is provided a condensed-cyclic compound represented by Formula 1 below:

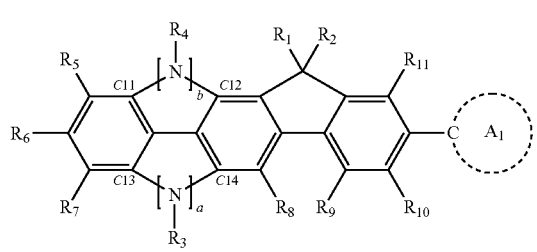

Formula 1 wherein either a=1 and b=0; or a=0 and b=1;

when a=1, b=0, —$R_{12}$ is connected to $C_{11}$, and $R_{13}$ is connected to $C_{12}$, and when a=0, b=1, —$R_{12}$ is connected to $C_{13}$, and $R_{13}$ is connected to $C_{14}$;

$A_1$ is a substituted or unsubstituted $C_6$-$C_{60}$ aryl group, a substituted or unsubstituted $C_2$-$C_{60}$ hetero cyclic group, a group represented by Formula 2A below, or a group represented by Formula 2B below:

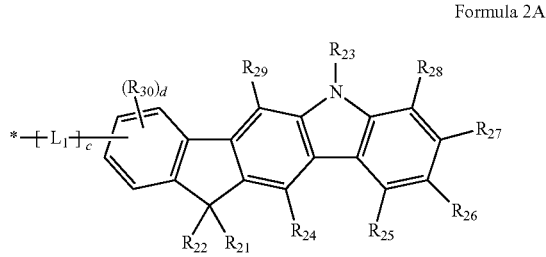

Formula 2A

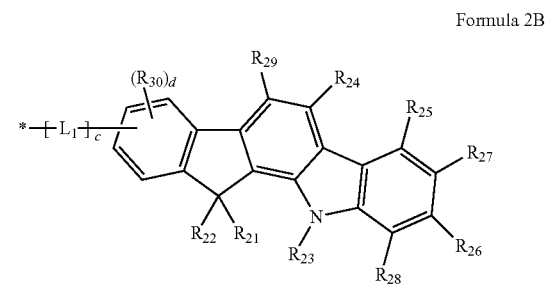

Formula 2B $L_1$ is a substituted or unsubstituted $C_6$-$C_{60}$ arylene group;

c is an integer from 0 to 5.

d is an integer from 1 to 4;

$R_1$ to $R_{13}$ and $R_{21}$ to $R_{30}$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ hetero cyclic group, —N($Q_1$)($Q_2$), —Si($Q_3$)($Q_4$)($Q_5$), a group represented by Formula 3A below, or a group represented by Formula 3B below:

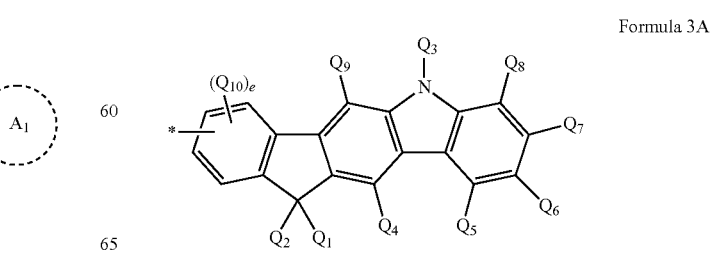

Formula 3A

-continued

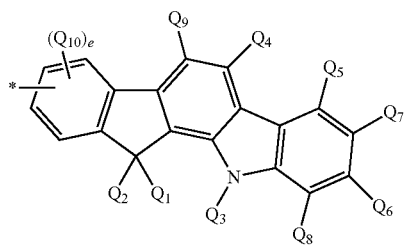

Formula 3B $Q_1$ to $Q_{10}$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ hetero cyclic group; and e is an integer from 1 to 4.

According to another aspect of the present invention, there is provided an organic light-emitting diode (OLED) including a first electrode, a second electrode disposed opposite to the first electrode; and a first layer interposed between the first electrode and the second electrode, wherein the first layer includes a condensed-cyclic compound of formula 1.

According to another aspect of the present invention, there is provided a flat panel display device including a transistor that includes a source, a drain, a gate, and an active layer and the OLED diode, wherein one of the source and the drain is electrically connected to the first electrode of the OLED.

BRIEF DESCRIPTION OF THE DRAWINGS

The above and other features and advantages of the present invention will become more apparent by describing in detail exemplary embodiments thereof with reference to the attached drawing in which.

DETAILED DESCRIPTION OF THE INVENTION

Figure 1:
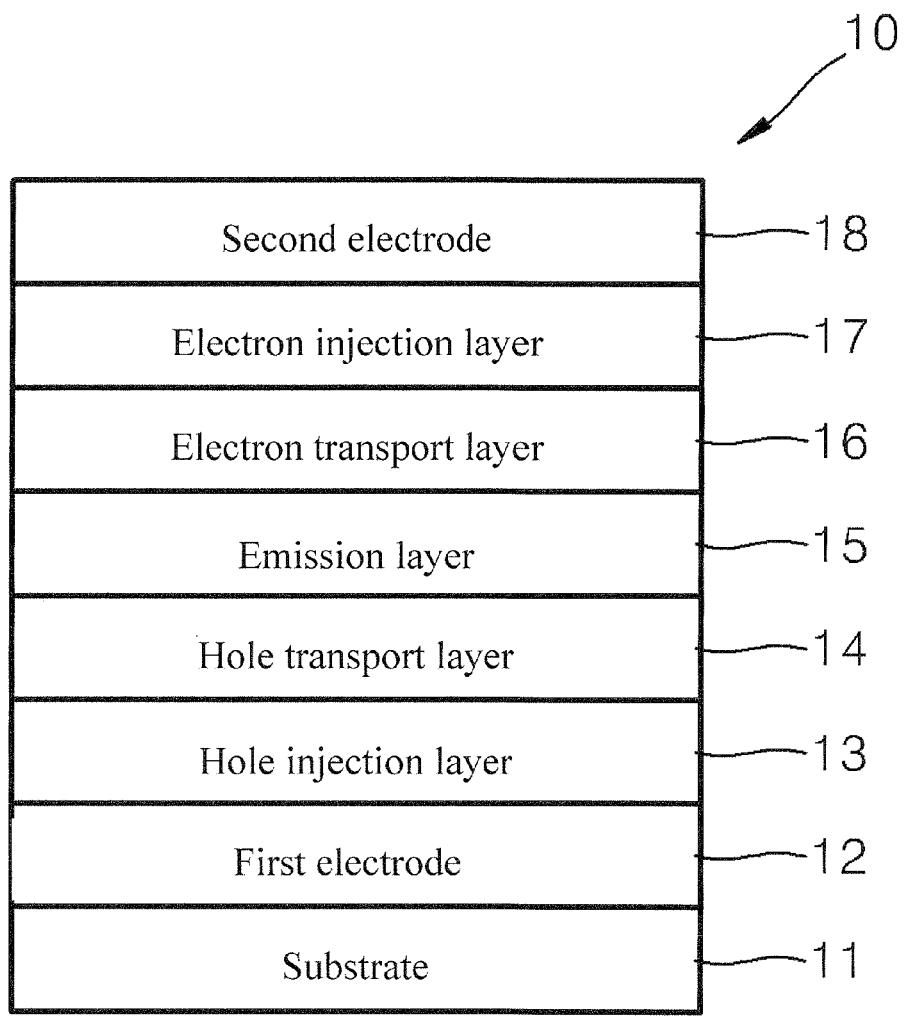
FIG. 1 is a schematic cross-sectional view of an organic light-emitting diode (OLED) according to an embodiment of the present invention.
Figure 2:
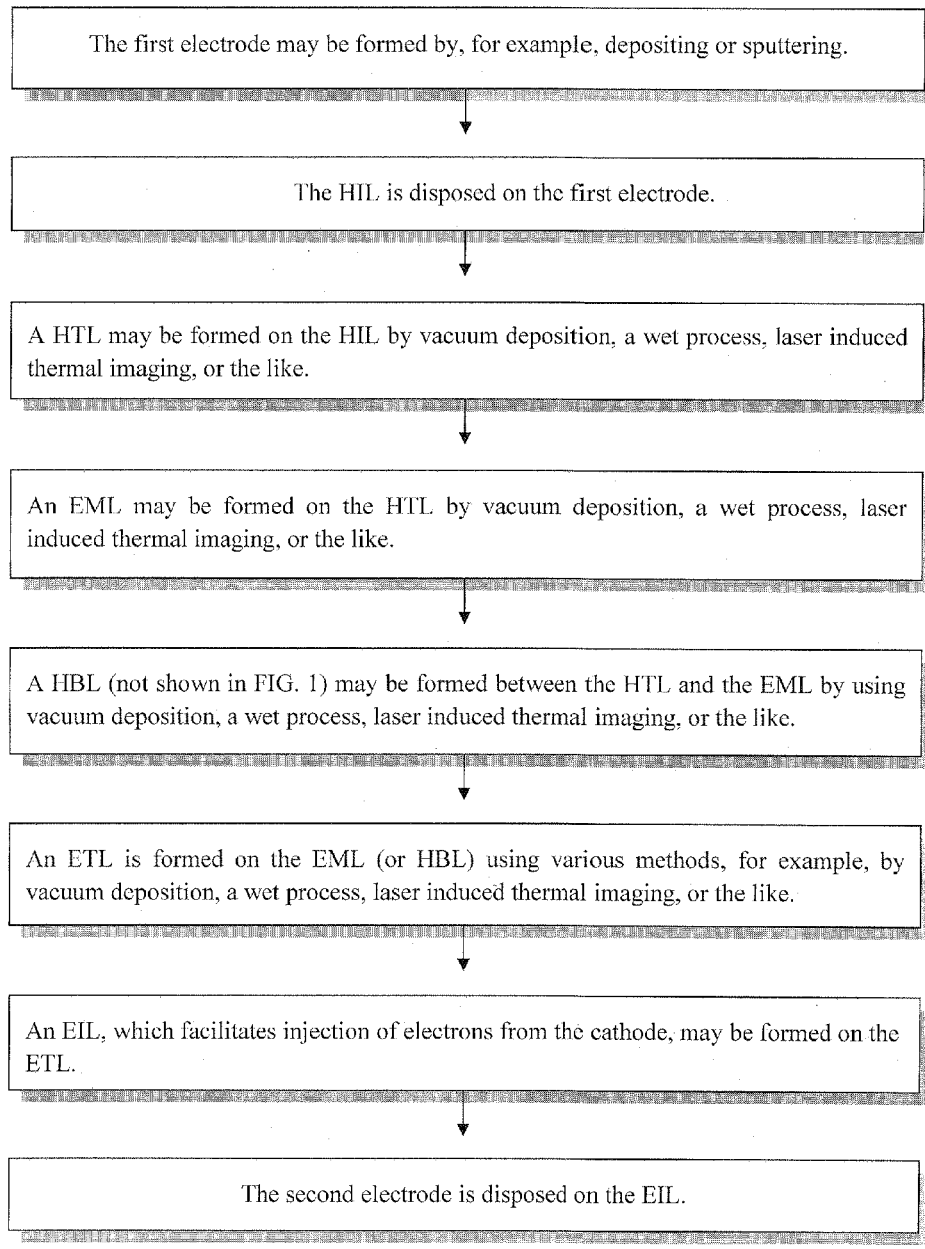
FIG. 2 shows a process for the preparation of an organic light-emitting diode of the present invention.

Hereinafter, the present invention will now be described more fully with reference to the accompanying drawings, in which exemplary embodiments of the invention are shown.

There is provided a condensed-cyclic compound represented by Formula 1 below:

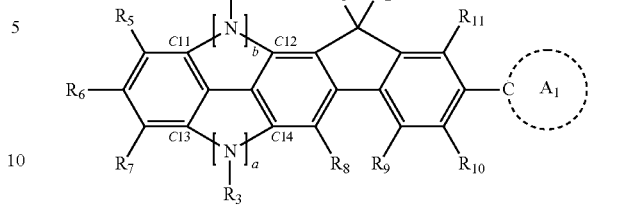

Formula 1

In Formula 1, when a=1, b=0, —$R_{12}$ may be connected to $C_{11}$, and $R_{13}$ may be connected to $C_{12}$. As a result, the condensed-cyclic compound may be represented by Formula 1A below:

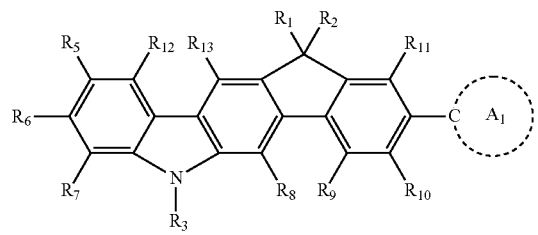

Formula 1A

Alternatively, in Formula 1, when a=0, b=1, —$R_{12}$ may be connected to $C_{13}$, and —$R_{13}$ may be connected to $C_{14}$. As a result, the condensed-cyclic compound may be represented by Formula 1B below:

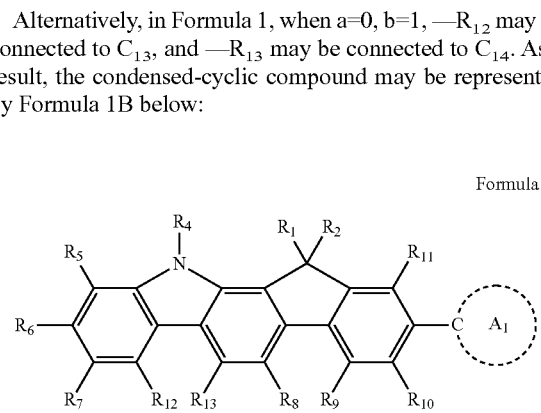

Formula 1B

In Formula 1, $A_1$ may be a substituted or unsubstituted $C_6$-$C_{60}$ aryl group or a substituted or unsubstituted $C_2$-$C_{60}$ hetero cyclic group.

For example, $A_1$ may be a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted dibenzopuranyl group, or a substituted or unsubstituted dibenzothiophenyl group, but is not limited thereto.

For example, $A_1$ may be a substituted or unsubstituted phenyl group, a substituted or unsubstituted naphthyl group, a substituted or unsubstituted fluorenyl group, a substituted or unsubstituted spiro-fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted carbazolyl group, a substituted or unsubstituted benzoimidazolyl group, a substituted or unsubstituted triazinyl group, a substituted or unsubstituted dibenzopuranyl group, a substituted or unsubstituted dibenzothiophenyl group, or a substituted or unsubstituted oxadiazolyl group.

In particular, $A_1$ may be selected from the group consisting of compounds represented by Formulae 5A to 5P below:

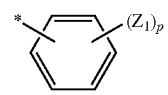

Formula 5A

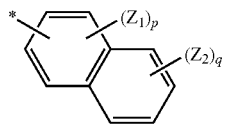

Formula 5B

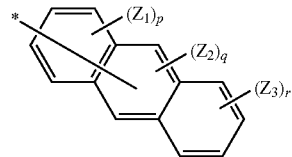

Formula 5C

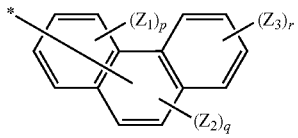

Formula 5D

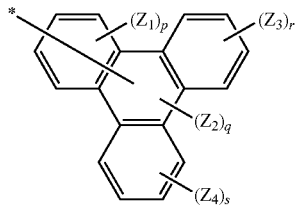

Formula 5E

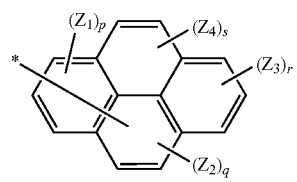

Formula 5F

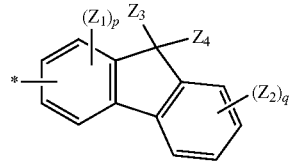

Formula 5G

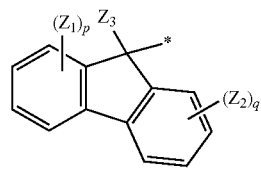

Formula 5H

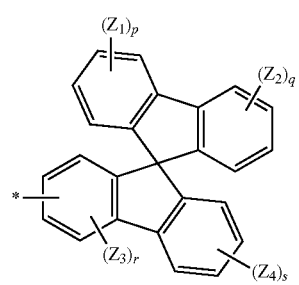

Formula 5I

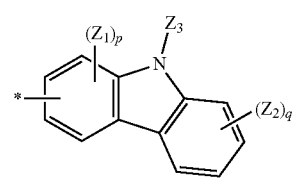

Formula 5J

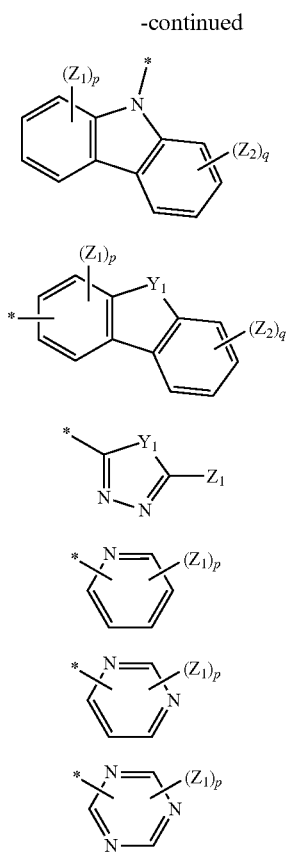

Formula 5K

Formula 5L

Formula 5M

Formula 5N

Formula 5O

Formula 5P

In Formulae 5A to 5P, p, q, r and s may be each independently an integer from 1 to 4.

In Formulae 5A to 5P, $Y_1$ may be O or S.

In Formulae 5A to 5P, $Z_1$ to $Z_4$ may be each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or to unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ hetero cyclic group, —N($Q_{11}$)($Q_{12}$), or —Si($Q_{13}$)($Q_{14}$)($Q_{15}$). In this regard, $Q_{11}$ to $Q_{15}$ may be each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ hetero cyclic group.

For example, $Z_1$ to $Z_4$ may be each independently a hydrogen atom, a heavy hydrogen atom, —F, a hydroxyl group, a cyano group, a nitro group, a carboxyl group, a substituted or unsubstituted $C_1$-$C_{10}$ alkyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted carbazolyl group, a substituted or unsubstituted benzoimidazolyl group, a substituted or unsubstituted triazinyl group, a substituted or unsubstituted dibenzopuranyl group, a substituted or unsubstituted dibenzothiophenyl group, a substituted or unsubstituted oxadiazolyl group, a substituted or unsubstituted imidazopyridinyl group, or —N($Q_{11}$)($Q_{12}$). In this regard, $Q_{11}$ to $Q_{12}$ may be each independently a hydrogen atom, a heavy hydrogen atom, a halogen atom, a hydroxyl group, a cyano group, a nitro group, a carboxyl group, a substituted or unsubstituted $C_1$-$C_{10}$ alkyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted carbazolyl group, a substituted or unsubstituted benzoimidazolyl group, a substituted or unsubstituted triazinyl group, a substituted or unsubstituted dibenzopuranyl group, a substituted or unsubstituted dibenzothiophenyl group, a substituted or unsubstituted oxadiazolyl group, or a substituted or unsubstituted imidazopyridinyl group.

According to an embodiment of the present invention, in Formulae 5A to 5P, $Z_1$ to $Z_4$ may be each independently a hydrogen atom; a heavy hydrogen atom; —F; a hydroxyl group; a cyano group; a nitro group; a carboxyl group; a methyl group; an ethyl group; a propyl group; a butyl group; a pentyl group; a phenyl group; a phenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a naphthyl group; a naphthyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; an anthryl group; an anthryl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a fluorenyl group; a fluorenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a spiro-fluorenyl group; a spiro-fluorenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a pyrenyl group; a pyrenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a carbazolyl group; a carbazolyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a benzoimidazolyl group; a benzoimidazolyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; an imidazopyridinyl group; or an imidazopyridinyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group, but are not limited thereto.

In Formulae 5A to 5P, $Z_1$ to $Z_4$ are each independently $N(Q_{11})(Q_{12})$, wherein $Q_{11}$ and $Q_{12}$ may be each independently a hydrogen atom; a heavy hydrogen atom; —F; a hydroxyl group; a cyano group; a nitro group; a carboxyl group; a methyl group; an ethyl group; a propyl group; a butyl group; a pentyl group; a phenyl group; a phenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a naphthyl group; a naphthyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; an anthryl group; an anthryl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a fluorenyl group; a fluorenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a spiro-fluorenyl group; a spiro-fluorenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a pyrenyl group; a pyrenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a carbazolyl group; a carbazolyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a benzoimidazolyl group; a benzoimidazolyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; an imidazopyridinyl group; or an imidazopyridinyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group, but are not limited thereto.

In Formulae 5A to 5P, $Z_1$ to $Z_4$ may be each independently selected from the group consisting of compounds represented by Formulae 6A to 6Z below, but are not limited thereto:

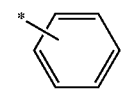

Formula 6A

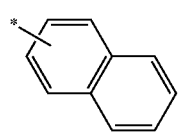

Formula 6B

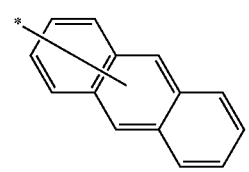

Formula 6C

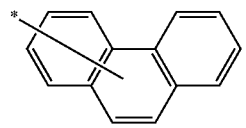

Formula 6D

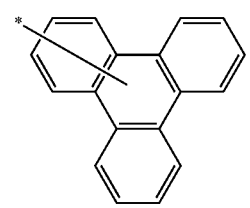

Formula 6E

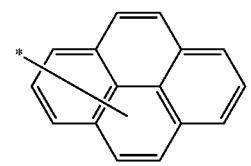

Formula 6F

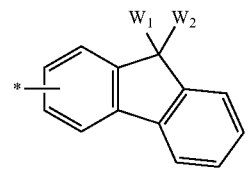

Formula 6G

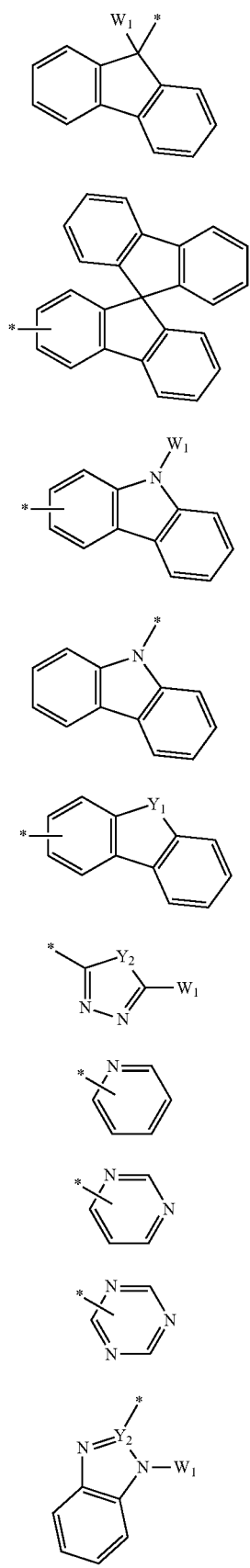
Formula 6H
Formula 6I
Formula 6J
Formula 6K
Formula 6L
Formula 6M
Formula 6N
Formula 6O
Formula 6P
Formula 6Q
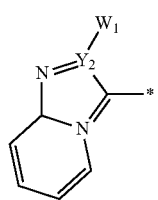
Formula 6R
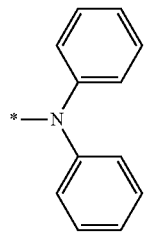
Formula 6S
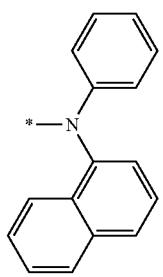
Formula 6T
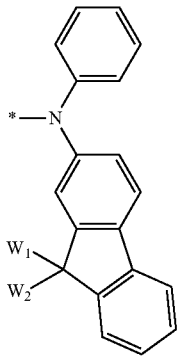
Formula 6U
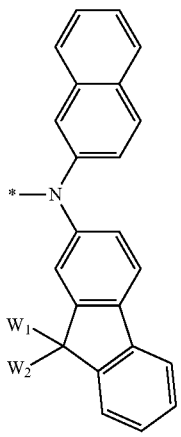
Formula 6V -continued Formula 6W

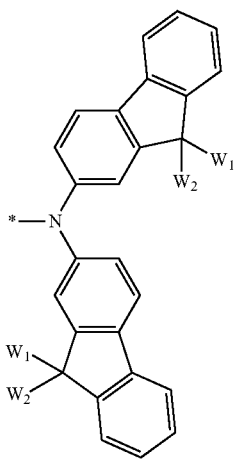

Formula 6X

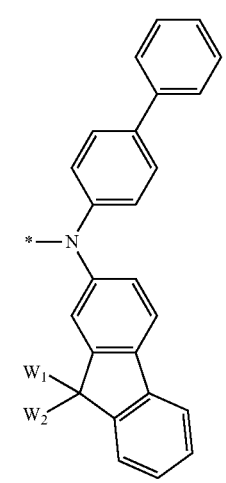

Formula 6Y

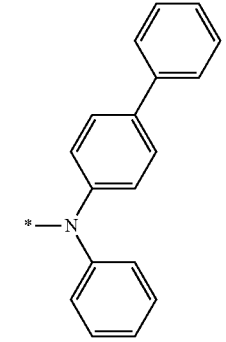

Formula 6Z

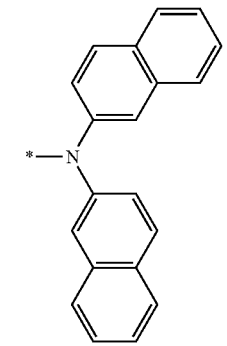

In Formulae 6A to 6Z, $W_1$ and $W_2$ may be each independently a hydrogen atom, a heavy hydrogen atom, a methyl group, an ethyl group, a propyl group, a butyl group, a pentyl group, a phenyl group, a naphthyl group, an anthryl group, or a carbazolyl group.

Meanwhile, in Formula 1, $A_1$ may be a group represented by Formula 2A below or a group represented by Formula 2B below:

Formula 2A

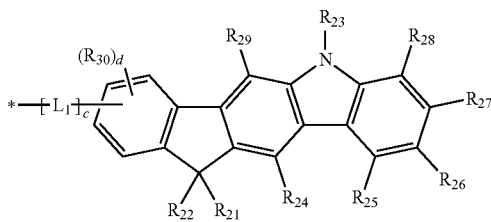

Formula 2B

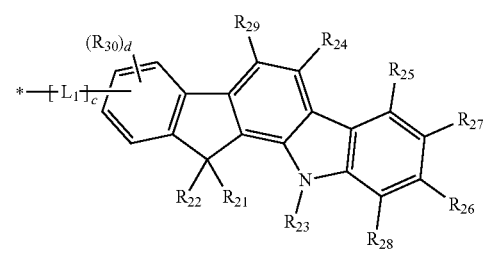

In Formulae 2A and 2B, $L_1$ may be a substituted or unsubstituted $C_6$-$C_{60}$ arylene group. For example, $L_1$ may be a substituted or unsubstituted phenylene group, a substituted or unsubstituted pentalenyl group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted spiro-fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrycenylene group, a substituted or unsubstituted naphthacenylene group, a substituted or unsubstituted pycenylene group, a substituted or unsubstituted perylenylene group, a substituted or unsubstituted pentaphenylene, group, or a substituted or unsubstituted hexacenylene group. For example, $L_1$ may be a phenylene group, but is not limited thereto.

In Formulae 3A and 3B, c may be an integer from 0 to 5. If c is 2 or greater, the $L_1$s may be the same or different. For example, c may be 0, 1 or 2. For example, c may be 0 or 1.

In Formulae 2A and 2B, d may be an integer from 1 to 4. If d is 2 or greater, the $R_{30}$s may be the same or different.

In Formulae 2A and 2B, $R_{21}$ to $R_{30}$ may be each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ hetero cyclic group, —N(Q$_1$)(Q$_2$), —Si(Q$_3$)(Q$_4$)(Q$_5$), a group represented by Formula 3A below, or a group represented by Formula 3B below:

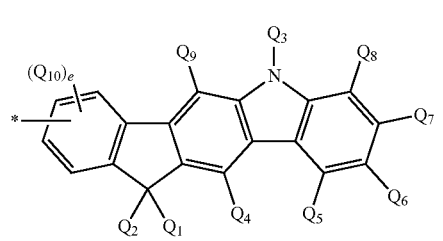

Formula 3A

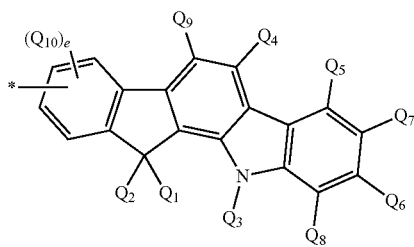

Formula 3B

In Formulae 3A and 3B, $Q_1$ to $Q_{10}$ may be each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ hetero cyclic group, and e is an integer from 1 to 4. In this regard, if e is 2 or greater, the $Q_{10}$s may be the same or different.

$R_{21}$ to $R_{30}$ may be each independently a hydrogen atom, a heavy hydrogen atom, a halogen atom, a hydroxyl group, a cyano group, a nitro group, a carboxyl group, a $C_1$-$C_{10}$ alkyl group, a substituted or unsubstituted phenyl group, a substituted or unsubstituted pentalenyl group, a substituted or unsubstituted indenyl group, a substituted or unsubstituted naphthyl to group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spirofluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyrimidinyl group, a substituted or unsubstituted pyridazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted dibenzofuranyl group, or a substituted or unsubstituted dibenzopuranyl group, —N(Q$_1$)(Q$_2$), a group represented by Formula 3A-1 below, or a group represented by Formula 3B-1 below:

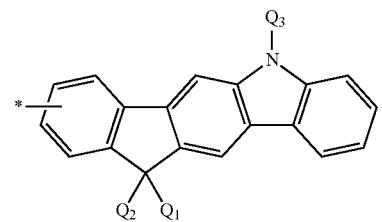

Formula 3A-1

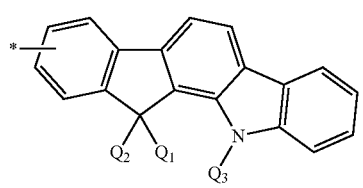

Formula 3B-1

$Q_1$ to $Q_3$ may be each independently a hydrogen atom, a heavy hydrogen atom, a halogen atom, a hydroxyl group, a cyano group, a nitro group, a carboxyl group, a $C_1$-$C_{10}$ alkyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spirofluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted dibenzofuranyl group, or a substituted or unsubstituted dibenzothiophenyl group.

For example, $A_1$ may be a group represented by Formula 2A-1 below or a group represented by Formula 2B-1 below:

Formula 2A-1

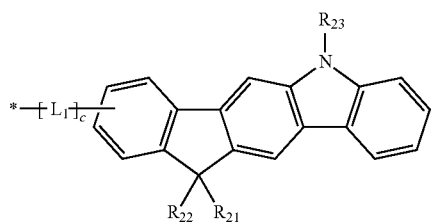

Formula 2B-1

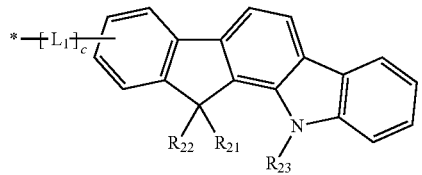

In Formulae 2A-1 and 2B-1, $L_1$, $R_{21}$-$R_{23}$ and a are defined as described above.

For example, $A_1$ is represented by Formula 2A-1 or 2B-1, wherein $R_{21}$ to $R_{23}$ may be each independently a hydrogen atom, a heavy hydrogen atom, a halogen atom, a hydroxyl group, a cyano group, a nitro group, a carboxyl group, a $C_1$-$C_{10}$ alkyl group, a substituted or unsubstituted phenyl group, a substituted or unsubstituted naphthyl group, a substituted or unsubstituted fluorenyl group, a substituted or unsubstituted spiro-fluorenyl group, a group represented by Formula 3A-1, or a group represented by Formula 3B-1. In this regard, in Formulae 3A-1 and 3B-1, $Q_1$ to $Q_3$ may be each independently a hydrogen atom, a heavy hydrogen atom, a halogen atom, a hydroxyl group, a cyano group, a nitro group, a carboxyl group, a $C_1$-$C_{10}$alkyl group, a substituted or unsubstituted phenyl group, a substituted or unsubstituted naphthyl group, a substituted or unsubstituted fluorenyl group, or a substituted or unsubstituted spiro-fluorenyl group.

According to another embodiment of the present invention, $A_1$ may be represented by Formula 2A-1 or 2B-1, wherein $L_1$ is a phenylene group; a is 0 or 1; and $R_{21}$ and $R_{22}$ may be each independently a hydrogen atom, a heavy hydrogen atom, a halogen atom, a hydroxyl group, a cyano group, a nitro group, a carboxyl group, a methyl group, an ethyl group, a propyl group, a butyl group, a pentyl group, a phenyl group, a naphthyl group and an anthryl group; $R_{23}$ may be a hydrogen atom, a heavy hydrogen atom, a halogen atom, a hydroxyl group, a cyano group, a nitro group, a carboxyl group, a methyl group, an ethyl group, a propyl group, a butyl group, a pentyl group, a phenyl group, a naphthyl group, an anthryl group, a group represented by Formula 3A-1, or a group represented by Formula 3B-1; wherein $Q_1$ to $Q_3$ may be each independently a hydrogen atom, a heavy hydrogen atom, a halogen atom, a hydroxyl group, a cyano group, a nitro group, a carboxyl group, a methyl group, an ethyl group, a propyl group, a butyl group, a pentyl group, a phenyl group, a naphthyl group, or an anthryl group.

In Formulae 1 and 2, $R_1$ to $R_{13}$ are defined as described above with reference to $R_{21}$.

For example, in Formulae 1 and 2, $R_1$ to $R_{13}$ may be each independently a hydrogen atom, a heavy hydrogen atom, —F, a hydroxyl group, a cyano group, a nitro group, a carboxyl group, a substituted or unsubstituted $C_1$-$C_{10}$ alkyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted carbazolyl group, a substituted or unsubstituted benzoimidazolyl group, a substituted or unsubstituted triazinyl group, a substituted or unsubstituted dibenzofuranyl group, a substituted or unsubstituted dibenzothiophenyl group, a substituted or unsubstituted oxadiazolyl group, or a substituted or unsubstituted imidazopyridinyl group.

In an embodiment of the present invention, $R_1$ to $R_{13}$ may be each independently a hydrogen atom; a heavy hydrogen atom; —F; a hydroxyl group; a cyano group; a nitro group; a carboxyl group; a methyl group; an ethyl group; a propyl group; a butyl group; a pentyl group; a phenyl group; a phenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a naphthyl group; a naphthyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; an anthryl group; an anthryl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a fluorenyl group; a fluorenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a spiro-fluorenyl group; a spiro-fluorenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a pyrenyl group; a pyrenyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a carbazolyl group; a carbazolyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; a benzoimidazolyl group; a benzoimidazolyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group; an imidazopyridinyl group; or an imidazopyridinyl group substituted with at least one selected from the group consisting of a heavy hydrogen atom, —F, a hydroxyl group, a cyano group, a nitro group, a carboxyl group, a methyl group, an ethyl group, a propyl group, a butyl group, a pentyl group, a phenyl group, a naphthyl group, an anthryl group, and a carbazolyl group.

For example, $R_1$ to $R_{13}$ may be each independently selected from the group consisting of compounds represented by Formulae 7A to 7O, but are not limited thereto.

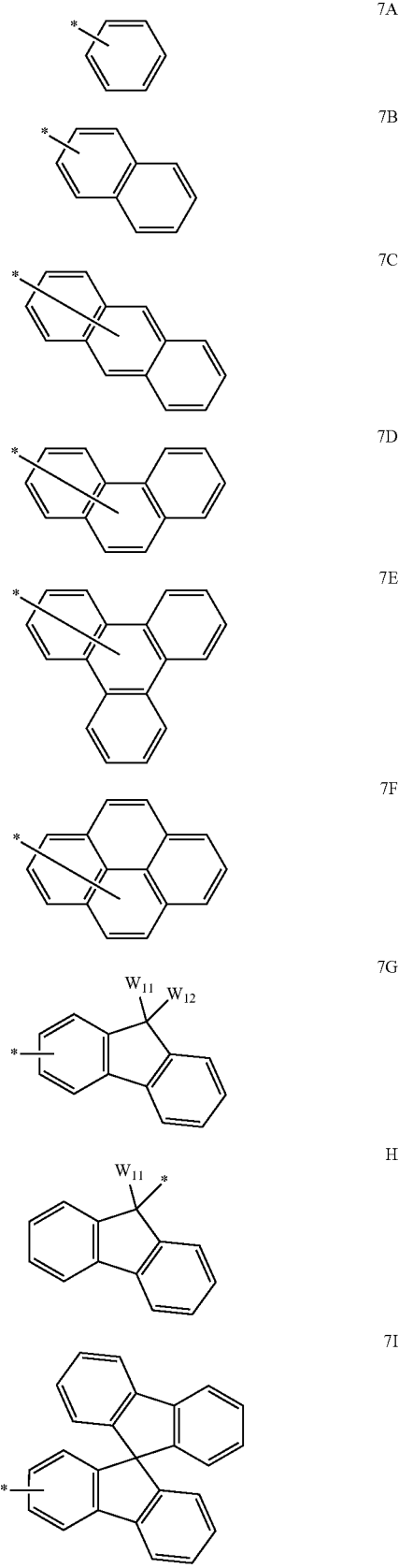

-continued

7J 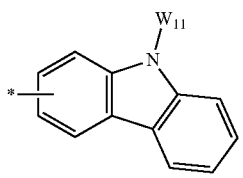

7K 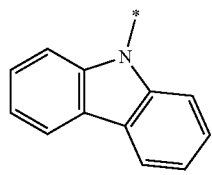

7L 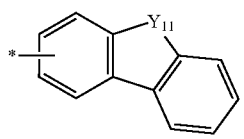

7M 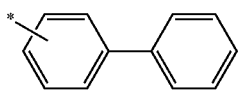

-continued

7N 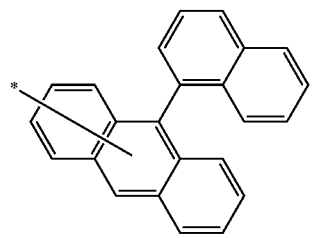

7O 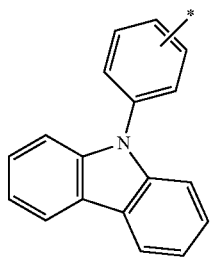

In Formulae 7A to 7O, $Y_{11}$ may be O or S; $W_{11}$ and $W_{12}$ may be each independently a hydrogen atom, a methyl group, an ethyl group, a propyl group, a butyl group, a pentyl group, a phenyl group, a naphthyl group, an anthryl group, or a carbazolyl group, but they are not limited thereto.

The condensed-cyclic compound may be any one selected from the group consisting of Compounds 1 to 65 below, but is not limited thereto:

1 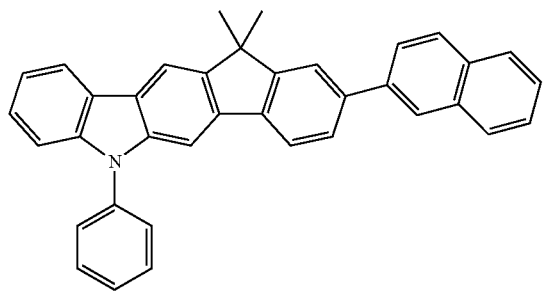

2 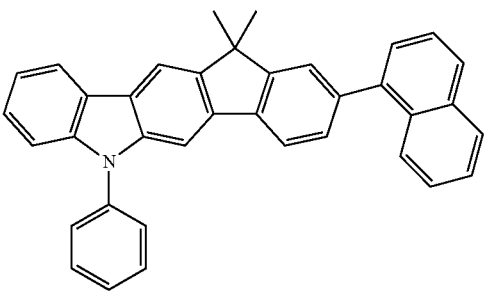

3 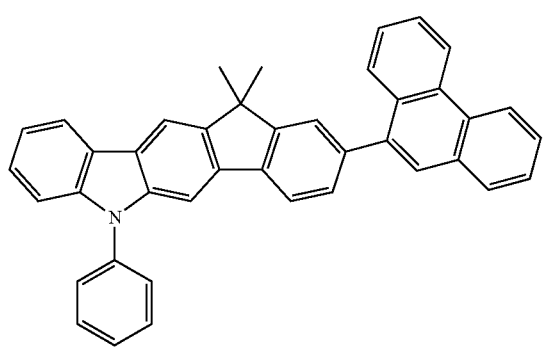

4 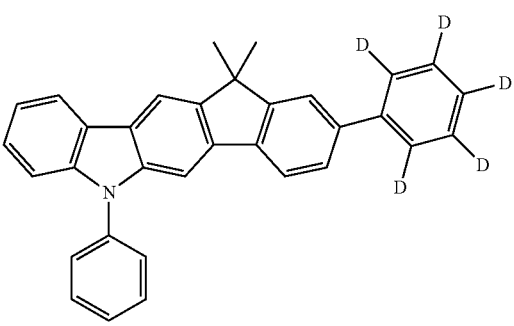

-continued
5
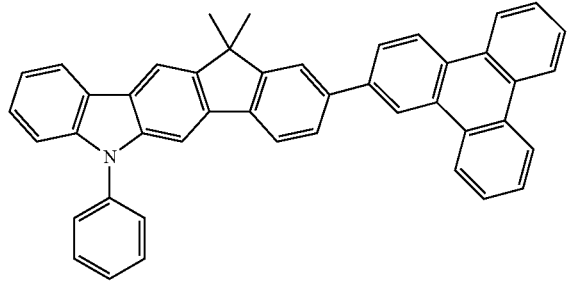
6
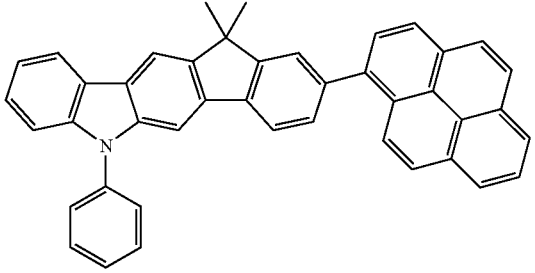
7
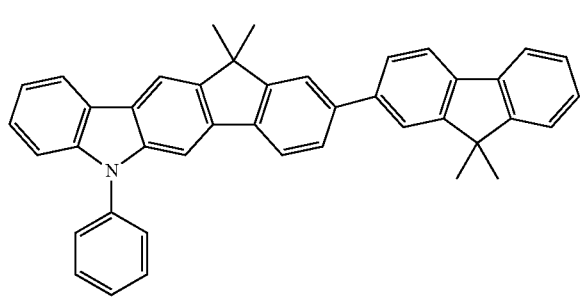
8
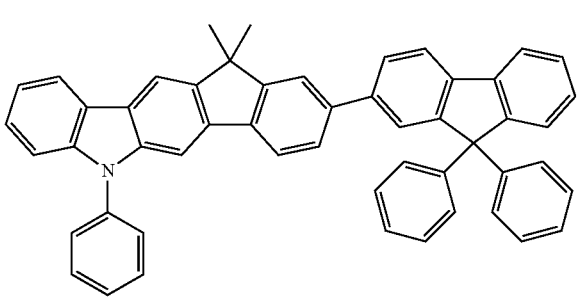
9
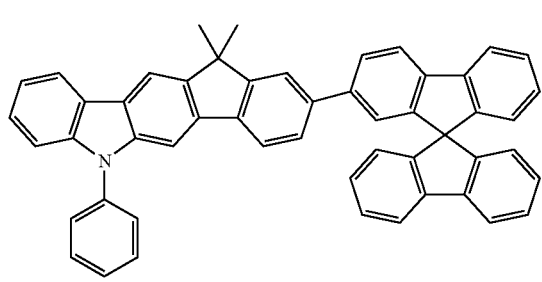
10
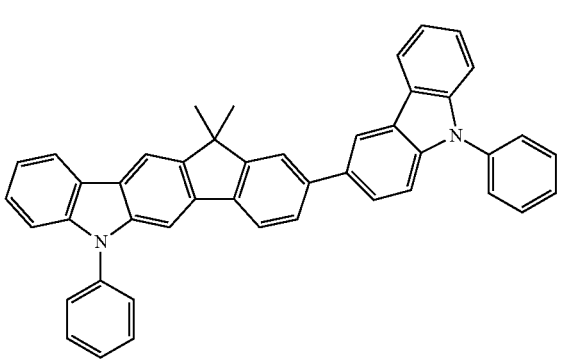
11
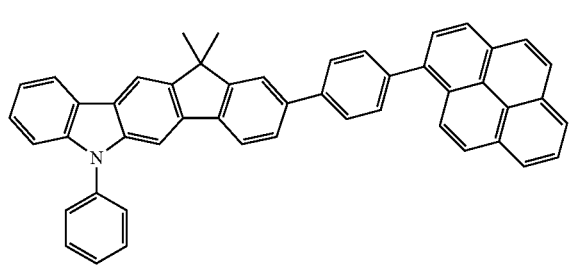
12
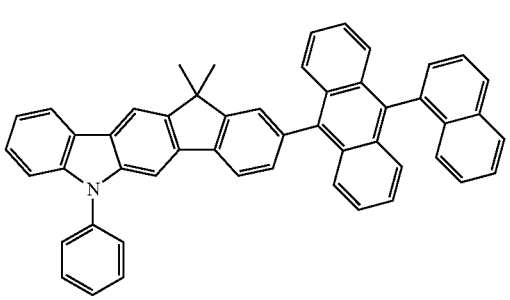
13
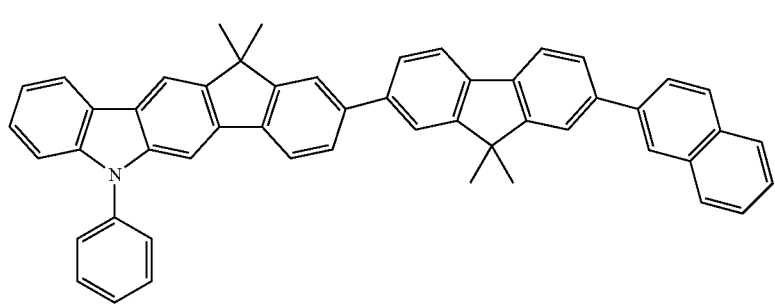

-continued
14
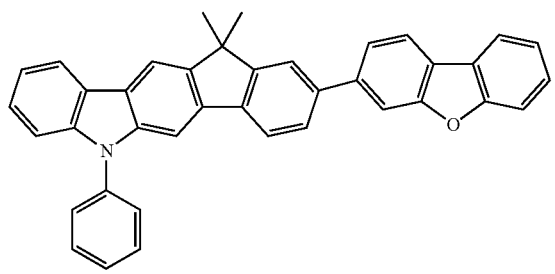
15
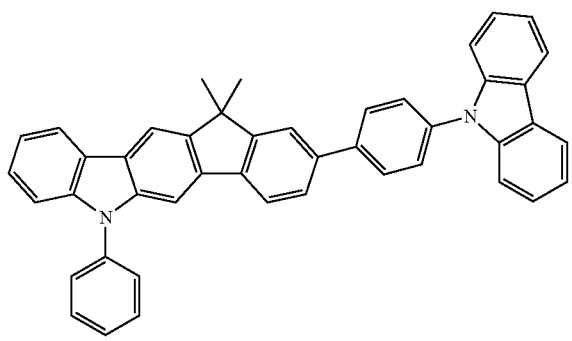
16
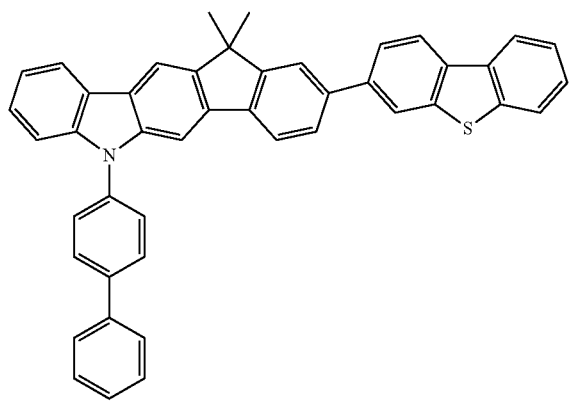
17
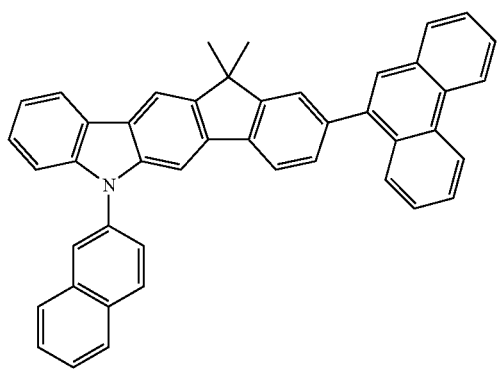
18
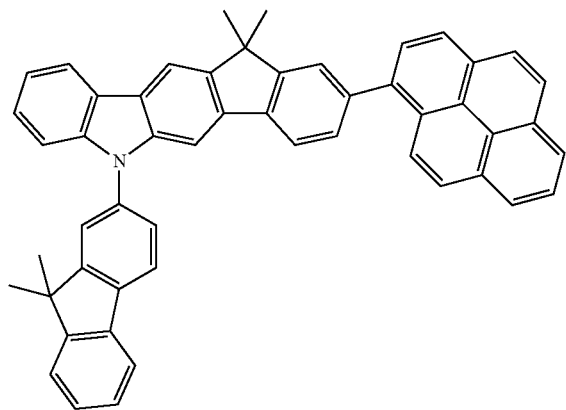
19
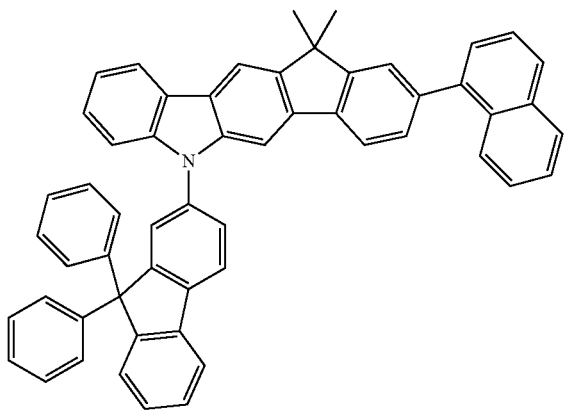
20
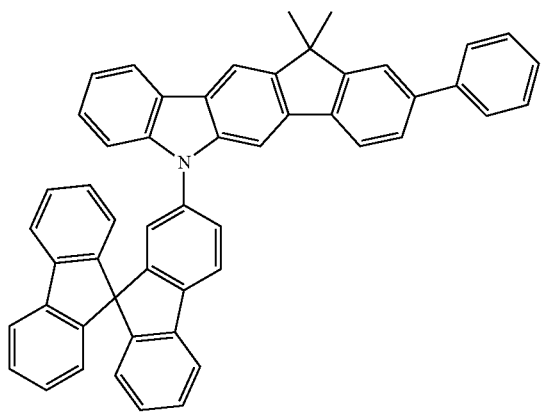
21
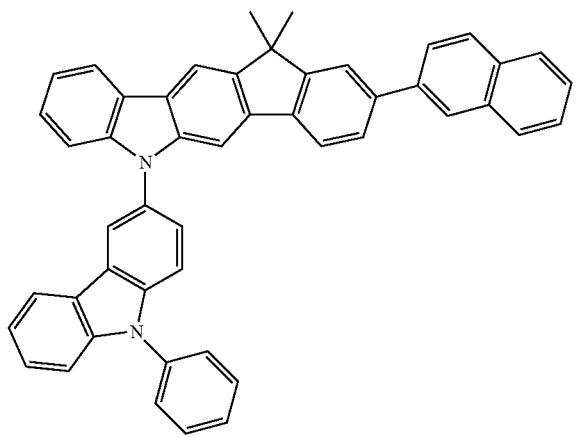

-continued
22
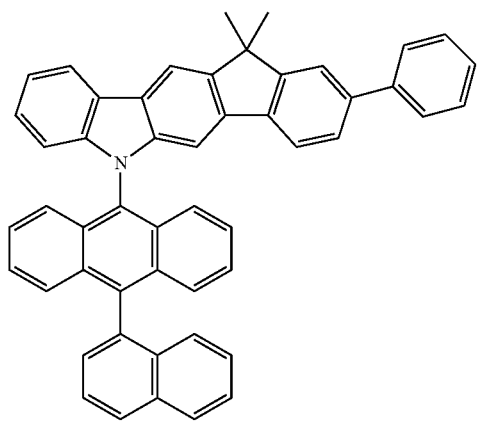
23
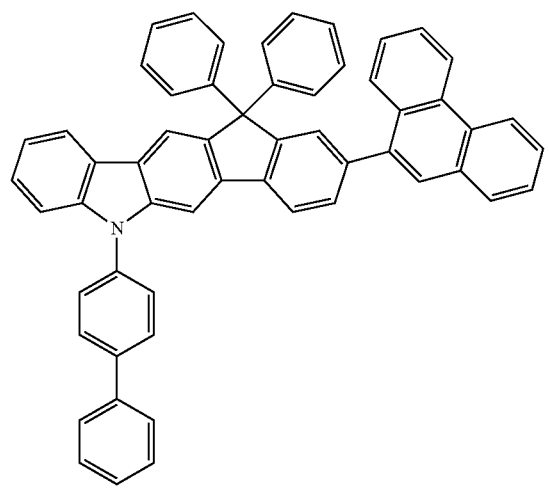
24
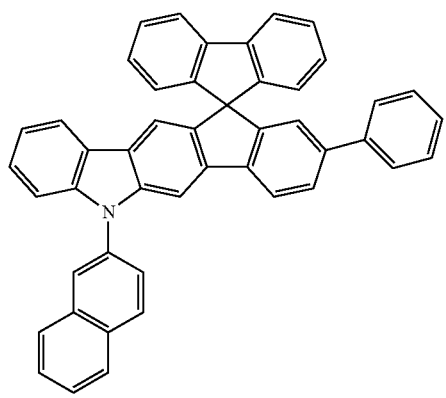
25
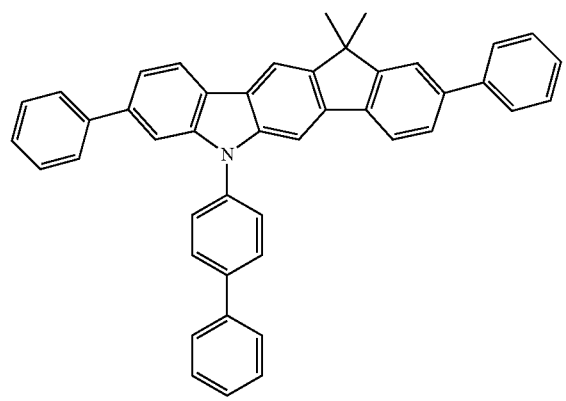
26
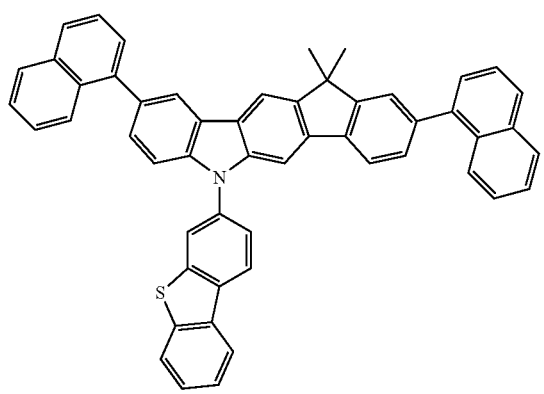
27
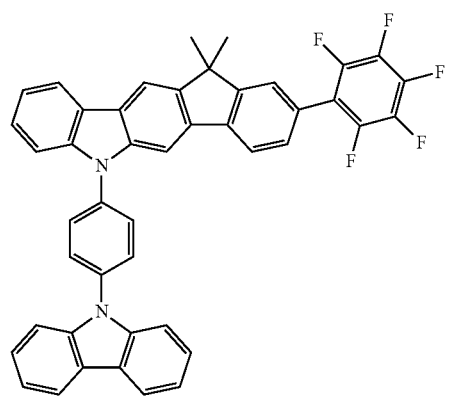
28
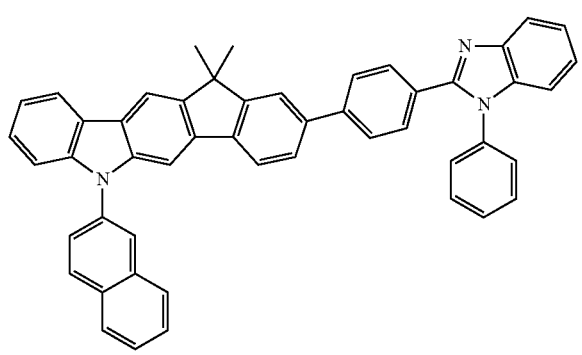
29
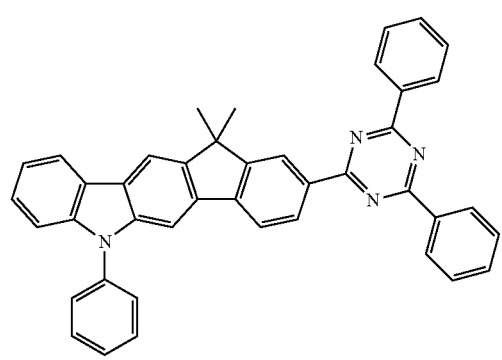

-continued
30
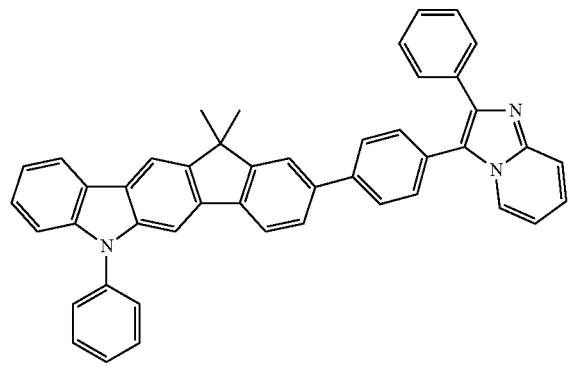
31
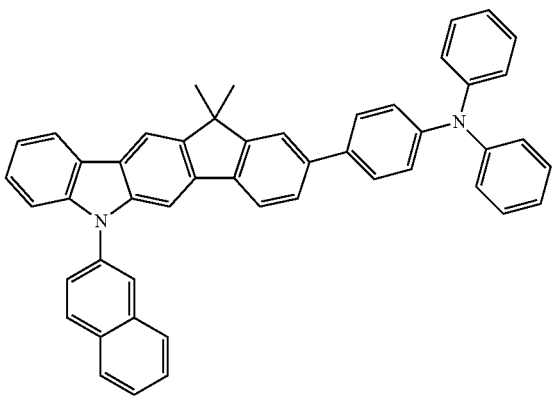
32
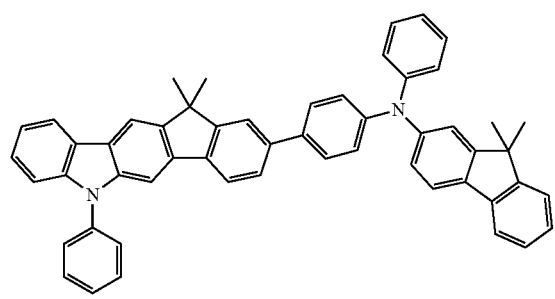
33
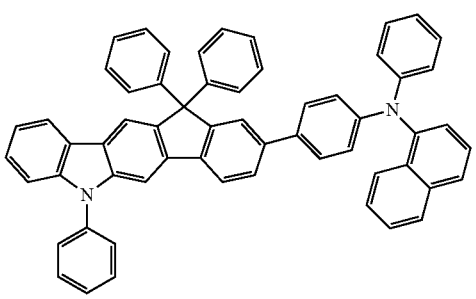
34
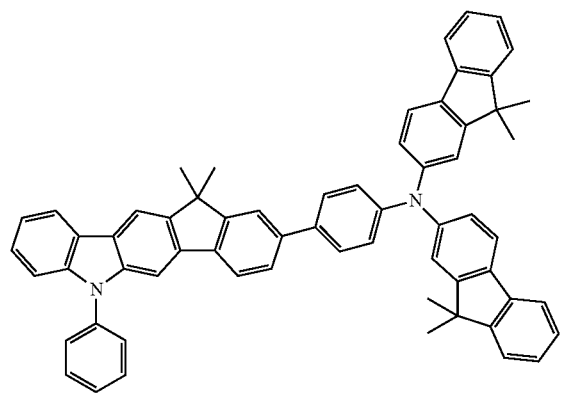
35
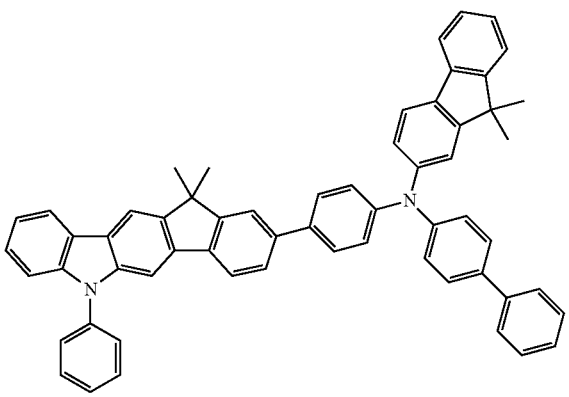
36
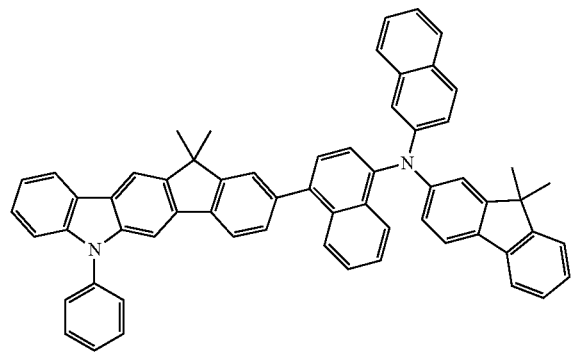
37
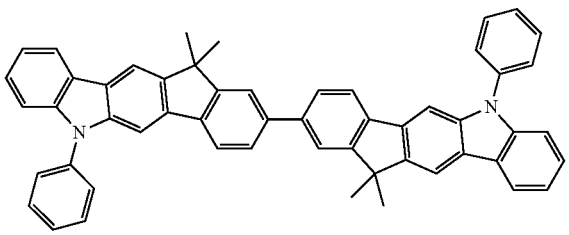

38
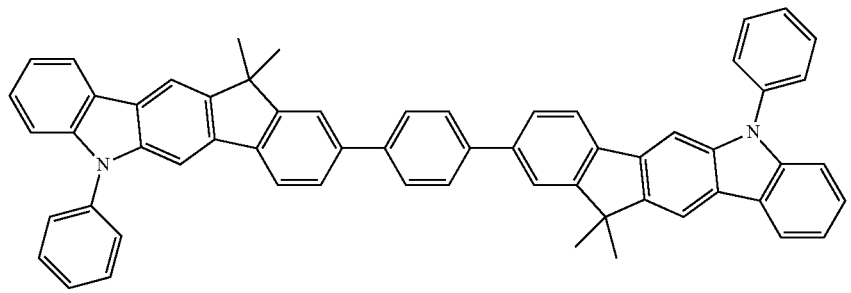
39
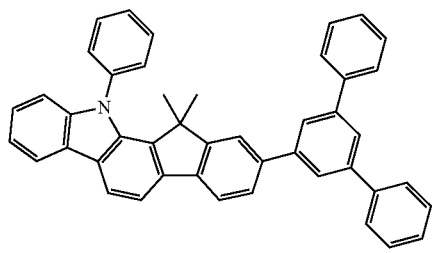
40
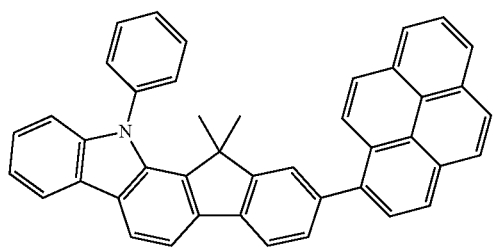
41
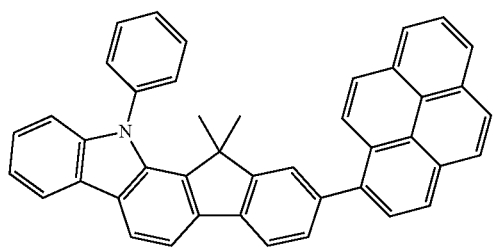
42
43
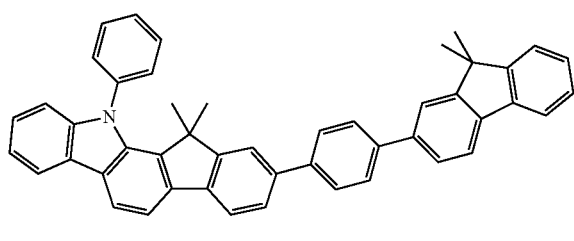
44
45
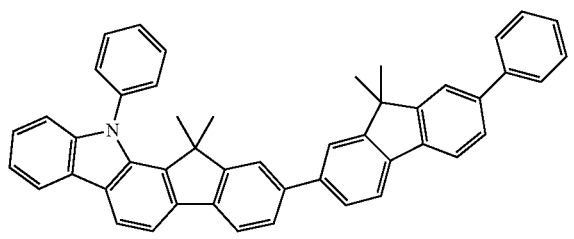
46
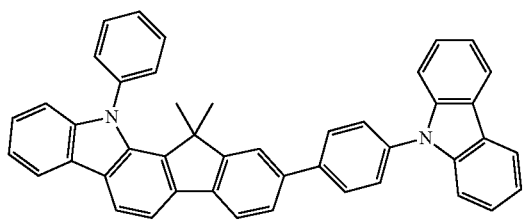

-continued
47
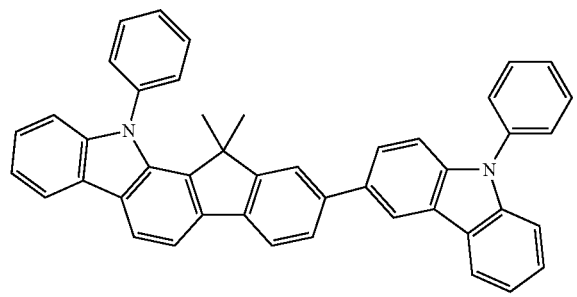
48
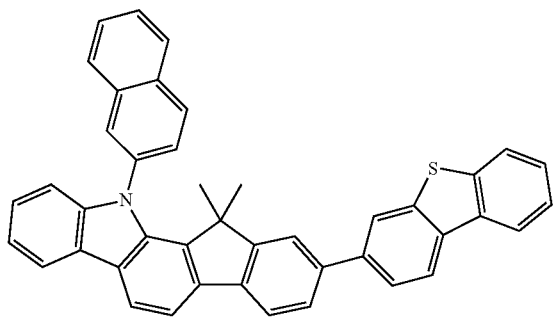
49
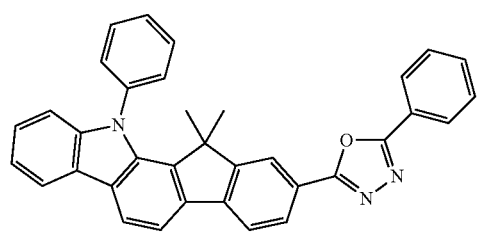
50
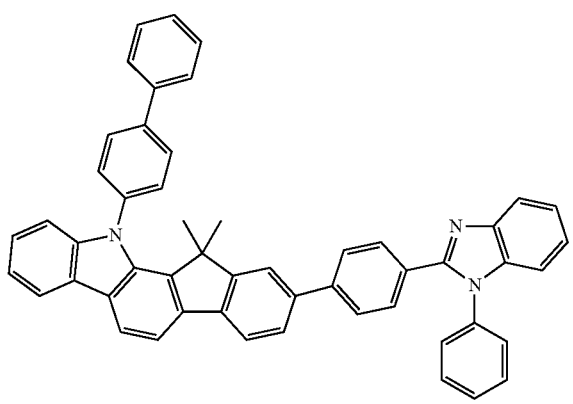
51
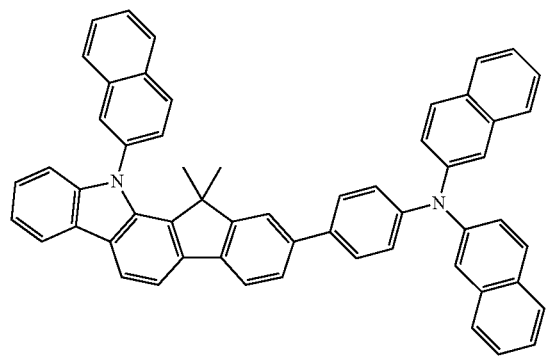
52
53
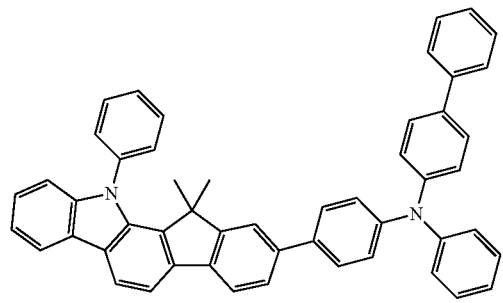
54
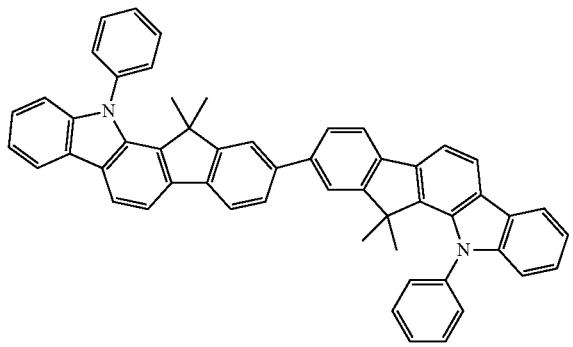

-continued
55
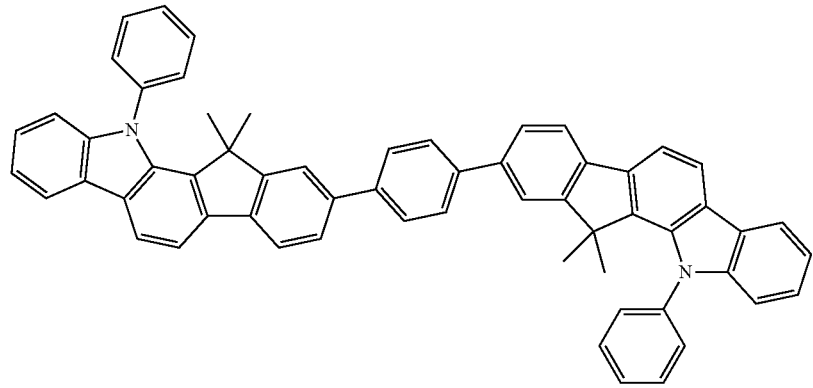
56
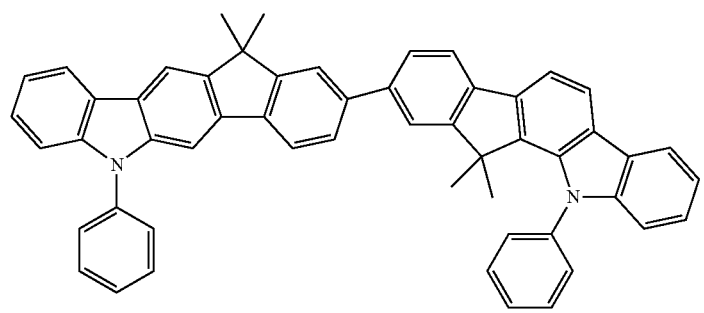
57
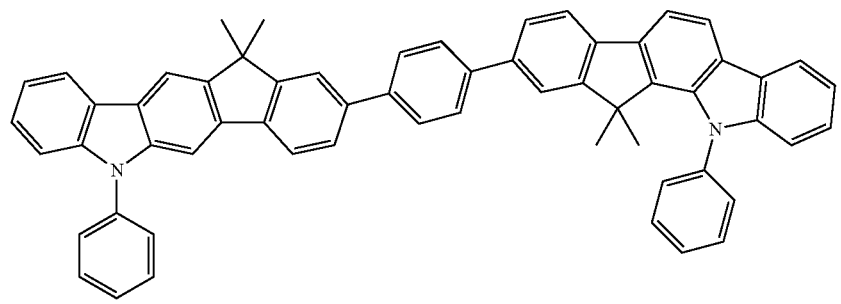
58
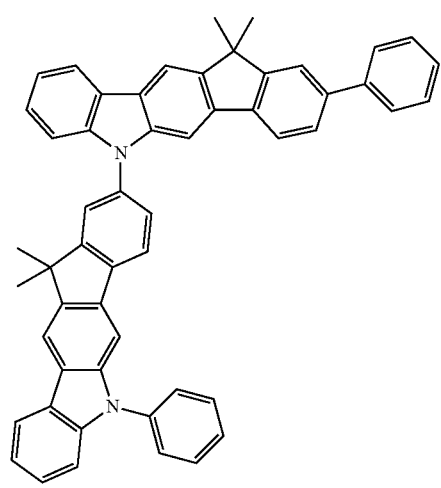
59
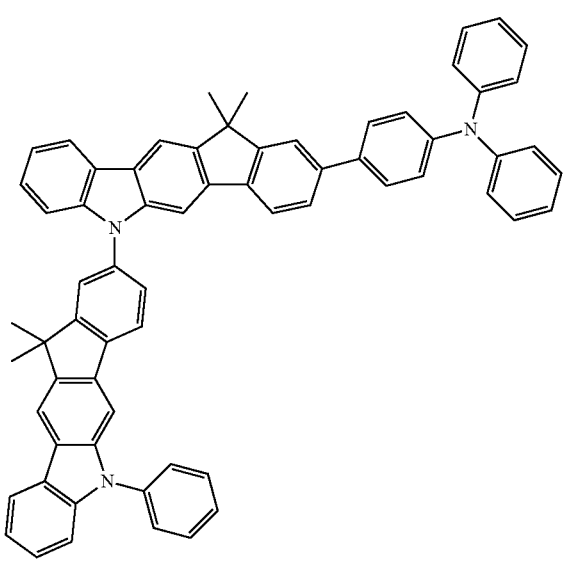

-continued
60
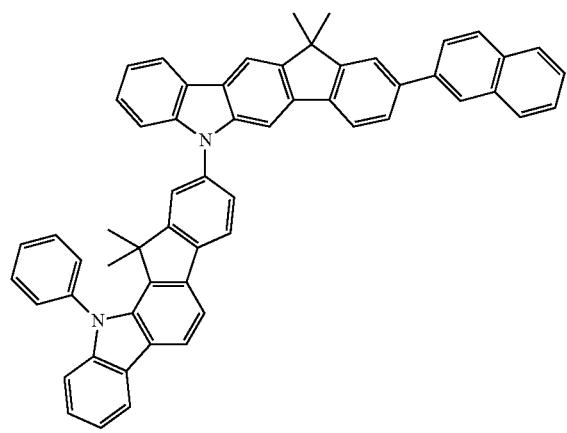
61
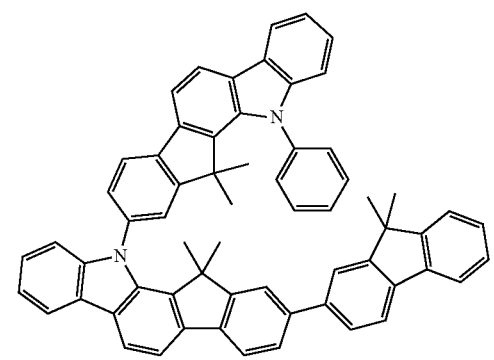
62
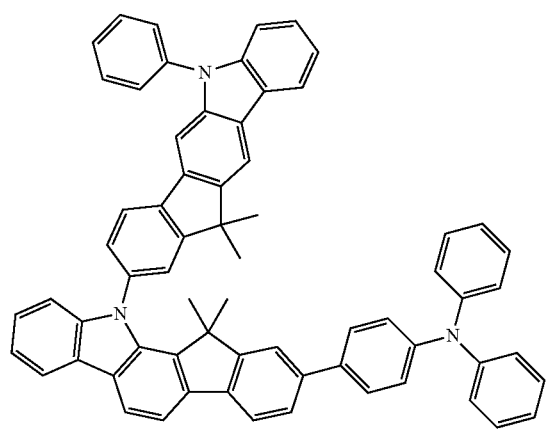
63
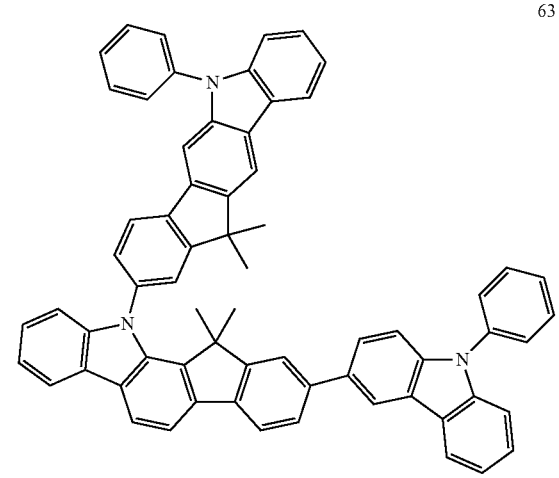
64
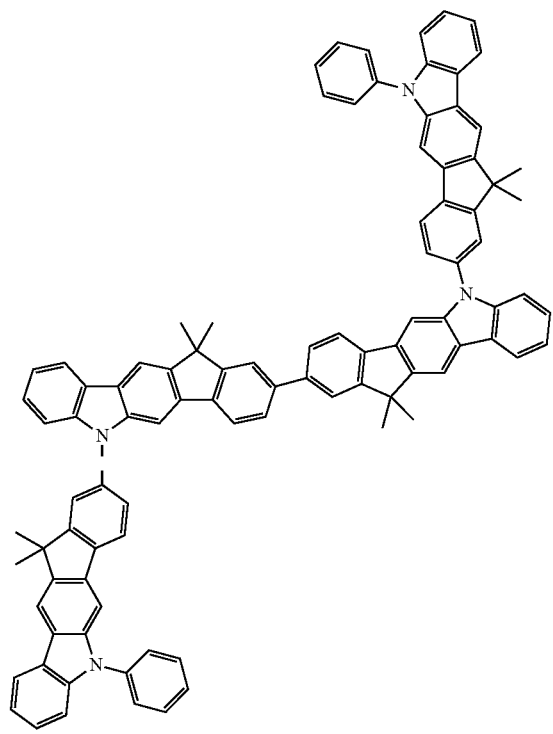

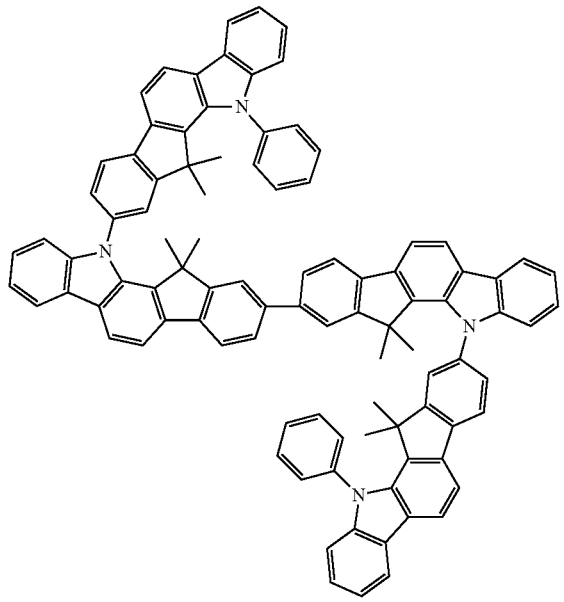

According to an embodiment of the present invention, the condensed-cyclic compound may be Compound 6, 8, 22, 27, 44, 35 or 52, but is not limited thereto.

The term "substituted A" in the "a substituted or unsubstituted A (A is any substituent)" used herein refers to A in which at least one hydrogen atom is substituted with one selected from the group consisting of a heavy hydrogen atom, a halogen atom, a hydroxyl group, a cyano group, an amidino group, a hydrazinyl group, a carboxylic acid group or a salt derivative thereof, a sulfonic acid group or a salt derivative thereof, a phosphoric acid group or a salt to derivative thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_2$-$C_{60}$ hetero cyclic group, —N($Q_{101}$)($Q_{102}$), and —Si($Q_{103}$)($Q_{104}$)($Q_{105}$). In this regard, $Q_{101}$ to $Q_{105}$ may be each independently a hydrogen atom, a halogen atom, a hydroxyl group, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, or a substituted or to unsubstituted $C_2$-$C_{60}$ hetero cyclic group. If there are 2 or more substituents, the substituents may be the same or different.

For example, the "substituted A" refers to A in which at least one hydrogen atom is substituted with at least one selected from the group consisting of a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{20}$ aryl group, a substituted or unsubstituted $C_2$-$C_{20}$ hetero cyclic group, —N($Q_{101}$)($Q_{102}$), and —Si($Q_{103}$)($Q_{104}$)($Q_{105}$), wherein $Q_{101}$ to $Q_{105}$ may be each independently a hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{20}$ aryl group, or a substituted or unsubstituted $C_2$-$C_{20}$ hetero cyclic group.

For example, the "substituted A" may be A in which at least one hydrogen atom is substituted with a heavy hydrogen atom, a halogen atom, a hydroxyl group, a cyano group, a methyl group, an ethyl group, a propyl group, a butyl group, a pentyl group, a methoxy group, an ethoxy group, a propoxy group, a pentoxy group, a phenyl group, a naphthyl group, or an anthryl group.

The unsubstituted $C_1$-$C_{60}$ alkyl group used herein may be a linear or branched group. Examples of the unsubstituted $C_1$-$C_{60}$ alkyl group include methyl, ethyl, propyl, isobutyl, sec-butyl, pentyl, iso-amyl, and hexyl. The substituents of the substituted $C_1$-$C_{60}$ alkyl group are defined as described above with reference to the "substituted A".

The unsubstituted $C_2$-$C_{60}$ alkenyl group used herein refers to a hydrocarbon chain having at least one carbon-carbon double bond at the center or at a terminal of the unsubstituted $C_2$-$C_{60}$ alkyl group. Examples of the unsubstituted $C_2$-$C_{60}$ alkenyl group are ethenyl, propenyl, butenyl, pnetenyl, hexenyl, heptenyl, octenyl, propadienyl, isoprenyl, and allyl. The substituents of the substituted $C_2$-$C_{60}$ alkenyl group are defined as described above with reference to the "substituted A".

The unsubstituted $C_2$-$C_{60}$ alkynyl group used herein refers to a hydrocarbon chain having at least one carbon-carbon triple bond at the center or at a terminal of the unsubstituted $C_2$-$C_{60}$ alkyl group. Examples of the unsubstituted $C_2$-$C_{60}$ alkynyl group include acetylenyl. The substituents of the substituted $C_2$-$C_{60}$ alkynyl group are defined as described above with reference to the "substituted A".

The unsubstituted $C_1$-$C_{60}$ alkoxy group used herein may be represented by —OY, to wherein Y is a unsubstituted $C_1$-$C_{60}$ alkyl group as described above, and may be methoxy, ethoxy, isopropyloxy, butoxy, or pentoxy. The substituents of the substituted $C_1$-$C_{60}$ alkoxy group are defined as described above with reference to the "substituted A".

The unsubstituted $C_3$-$C_{60}$ cycloalkyl group used herein refers to a cyclic saturated hydrocarbon chain, and may be cyclopropyl, cyclobutyl, cyclopentyl, cyclohexyl, or cyclooctyl. The substituents of the substituted $C_1$-$C_{60}$ cycloalkyl group are defined as described above with reference to the "substituted A".

The unsubstituted $C_3$-$C_{60}$ cycloalkenyl group used herein refers to a cyclic unsaturated hydrocarbon chain that has at least one carbon-carbon double bond and is not an aromatic ring, and examples of the unsubstituted $C_3$-$C_{60}$ cycloalkenyl group may be cyclopropenyl, cyclobutenyl, cyclopentenyl, cyclohexenyl, cycloheptenyl, 1,3-cyclohexadienyl, 1,4-cyclohexadienyl, 2,4-cycloheptadienyl, and 1,5-cyclooctadienyl. The substituents of the substituted $C_3$-$C_{60}$ cycloalkenyl group are defined as described above with reference to the "substituted A".

The unsubstituted $C_6$-$C_{60}$ aryl group used herein refers to a monocyclic or polycyclic monovalent group including a $C_6$-$C_{60}$ carbocyclic aromatic system. If the unsubstituted $C_6$-$C_{60}$ aryl group is a polycyclic group, at least two rings thereof may be fused to each other. Examples of the unsubstituted $C_6$-$C_{60}$ aryl group are a phenyl group, a pentalenyl group, an indenyl group, a naphthyl group, an azulenyl group, a heptalenyl group, an indacenyl group, an acenaphtyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl group, and a hexacenyl group. The substituents of the substituted $C_6$-$C_{60}$ aryl group are defined as described above with reference to the "substituted A".

The unsubstituted $C_6$-$C_{60}$ arylene group used herein refers to a monocyclic or polycyclic divalent group including a $C_6$-$C_{60}$ carbocyclic aromatic system, and examples of the unsubstituted $C_6$-$C_{60}$ arylene group are defines as described above with reference to the unsubstituted $C_6$-$C_{60}$ aryl group. The substituents of the substituted $C_6$-$C_{60}$ arylene group are defined as described above with reference to the "substituted A".

The unsubstituted $C_2$-$C_{60}$ hetero cyclic group used herein refers to a monocyclic or polycyclic group including at least one hetero atom selected from the group consisting of N, O, to P, and S. If the unsubstituted $C_2$-$C_{60}$ hetero cyclic group is a polycyclic group, at least two rings thereof may be fused to each other. Examples of the unsubstituted $C_2$-$C_{60}$ hetero cyclic group are a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, and a benzooxazolyl group. The substituents of the substituted $C_6$-$C_{60}$ hetero cyclic group are defined as described above with reference to the "substituted A".

The unsubstituted $C_6$-$C_{60}$ hetero cyclic divalent group used herein refers to a monocyclic or polycyclic divalent group including at least one hetero atom selected from the group consisting of N, O, P, and S. Examples of the unsubstituted $C_6$-$C_{60}$ hetero cyclic divalent group are defined with reference to the $C_6$-$C_{60}$ hetero cyclic group. The substituents of the substituted $C_6$-$C_{60}$ hetero cyclic divalent group are defined as described above with reference to the "substituted A".

The condensed-cyclic compound represented by Formula 1 may be synthesized using known organic synthesis methods. The method of synthesizing the condensed-cyclic compound will be obvious to one or ordinary skill in the art and will be described later in regard to reference examples.

The condensed-cyclic compound of Formula 1 may be used in an organic light-emitting diode (OLED). Accordingly, an OLED according to an embodiment or the present invention includes a first electrode, a second electrode disposed opposite to the first electrode, and a first layer interposed between the first electrode and the second electrode, wherein the first layer includes the condensed-cyclic compound represented by Formula 1.

The OLED may further include at least one layer selected from the group consisting of a hole injection layer (HIL), a hole transport layer (HTL), an emission layer (EML), a hole blocking layer (HBL), an electron transport layer (ETL) and an electron injection layer (EIL) between the first electrode and the second electrode in addition to the first layer. For example, the OLED may have a first electrode/HIL/HTL/first layer including the condensed-cyclic compound (i.e., as an EML)/ETL/EIL/second electrode structure, but the structure is not limited thereto.

The layers interposed between the first electrode and the second electrode (for example, i) the first layer and ii) at least one layer selected from the group consisting of the HIL, is the HTL, the EML, the HBL, the ETL, and the EIL in addition to the first layer) may be formed by deposition or a wet process.

The "wet process" is a process by which a mixture containing a material and a solvent is provided to a substrate, and at least one portion of the solvent is removed by drying and/or heat-treatment to form a layer including the material on the substrate.

For example, the first layer may be formed by using a known deposition method. Alternatively, a mixture including the condensed-cyclic compound and a solvent is provided to a region where the first layer will be formed (e.g., on the HTL) by spin coating, spraying, inkjet printing, dipping, casting, gravure coating, bar coating, roll coating, wire-bar coating, screen coating, flexo coating, offset coating, laser induced thermal imaging, or the like, and the mixture is dried and/or heat-treated to remove at least one portion of the solvent to form the first layer.

Meanwhile, the laser induced thermal imaging including forming the first layer by using a wet process as described above on a base film and transferring the first layer to a region where the first layer will be formed (e.g., on the HTL) by using a laser beam may also be used.

The first layer may be a hole injection layer, a hole transport layer, or a single layer having both hole injecting and hole transporting capabilities.

The first layer may also be an electron injection layer, an electron transport layer, or a single layer having both electron injecting and electron transporting capabilities.

Meanwhile, the first layer may be an EML. If the first layer is an EML, the first layer may only include the condensed-cyclic compound or may further include another compound in addition to the condensed-cyclic compound.

For example, the first layer may be an EML, and the condensed-cyclic compound contained in the first layer may be used as a fluorescent host or a phosphorescent host. In this regard, the first layer may further include a fluorescent dopant or a phosphorescent dopant. In particular, the first layer may be an EML including the condensed-cyclic compound functioning as a fluorescent host and a fluorescent dopant or an EML including the condensed-cyclic compound functioning as a phosphorescent host and a phosphorescent dopant.

Alternatively, the first layer may be an EML, and the condensed-cyclic compound contained in the first layer may be used as a fluorescent dopant. In this regard, the first layer may further include a fluorescent host or a phosphorescent host. In particular, the first layer may be an EML including i) the condensed-cyclic compound functioning as a fluorescent dopant and ii) host for a fluorescence or phosphorescence.

Meanwhile, the first layer of the OLED may be an EML, HTL or ETL, wherein the first layer may further include anthracene-based, arylamine-based and styryl-based compounds in addition to the condensed-cyclic compound.

In addition, the first layer of the OLED may be a HTL or ETL, wherein an EML is further interposed between the first electrode and the second electrode, wherein the EML includes at least one region selected from the group consisting of a red emission region, a green emission region, a blue emission region and a white emission region. At least one of the red emission region, the green emission region, the blue emission region and the white emission region may include a phosphorescent compound. The red emission region, the green emission region, the blue emission region, and the white emission region may be patterned by using a known method for a full color image or white emission. The phosphorescent compound may be selected from the group consisting of known phosphorescent hosts and phosphorescent dopants.

FIG. 1 is a schematic cross-sectional view of an OLED 10 according to an embodiment of the present invention. Hereinafter, the OLED 10 and a method of fabricating the OLED 10 will be described with reference to FIG. 1.

The OLED 10 includes a substrate 11, a first electrode 12, a hole injection layer (HIL) 13, a hole transport layer (HTL) 14, an emission layer (EML) 15, an electron transport layer (ETL) 16, an electron injection layer (EIL) 17, and a second electrode 18, which are sequentially stacked.

The substrate 11, which may be any substrate that is used in conventional OLEDs, may be a glass substrate or a transparent plastic substrate with excellent mechanical strength, thermal stability, transparency, surface smoothness, ease of handling, and water resistance.

The first electrode 12 may be formed by depositing or sputtering a material that is used to form the first electrode 12 on the substrate 11. When the first electrode 12 constitutes an anode, the material used to form the first electrode 12 may be a high work-function material so as to facilitate hole injection. The first electrode 12 may be a reflective electrode or a transmission electrode. Transparent and conductive materials such as ITO, IZO, $SnO_2$, and ZnO may be used to form the first electrode 12. The first electrode 12 may also be formed as a reflective electrode using magnesium (Mg), aluminum (Al), aluminum-lithium (Al—Li), calcium (Ca), magnesium-indium (Mg—In), magnesium-silver (Mg—Ag), or the like. The first electrode 12 may include two different materials. For example, the first electrode 12 may have a double layered structure with two different materials.

The HIL 13 is disposed on the first electrode 12.

The HIL 13 may be formed on the first electrode 12 by vacuum deposition, a wet process, laser induced thermal imaging, or the like.

When the HIL 13 is formed using vacuum deposition, the deposition conditions may vary according to a compound that is used to form the HIL 13, and the structure and thermal characteristics of the HIL 13 to be formed. For example, the deposition conditions may include a deposition temperature of about 100 to about 500° C., a vacuum pressure of about $10^{-8}$ to about $10^{-3}$ torr, and a deposition rate of about 0.01 to about 100 Å/sec, but are not limited thereto.

When the HIL 13 is formed using spin coating as a wet process, coating conditions may vary according to a compound that is used to form the HIL 13, and the structure and thermal properties of the HIL 13 to be formed. For example, the coating conditions may include a coating speed of about 2000 rpm to about 5000 rpm, and a thermal treatment temperature of about 80° C. to about 20° C., wherein the thermal treatment is for removing a solvent after coating. However, the coating conditions are not limited thereto.

The HIL 13 may be formed of the condensed-cyclic compound. Alternatively, widely-known HIL materials may also be used. Examples of such HIL materials include, but are not limited to, a phthalocyanine compound such as copper phthalocyanine, m-MTDATA represented by the formula shown below, TDATA represented by the formula shown below, 2-TNATA represented by the formula shown below, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and (polyaniline)/poly(4-styrenesulfonate) (PANI/PSS).

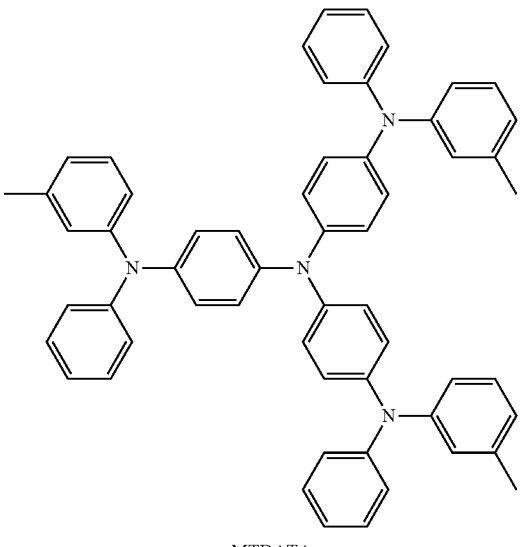

m-MTDATA

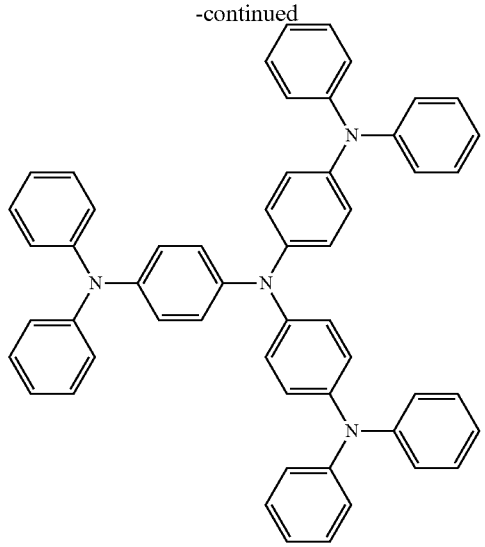

TDATA

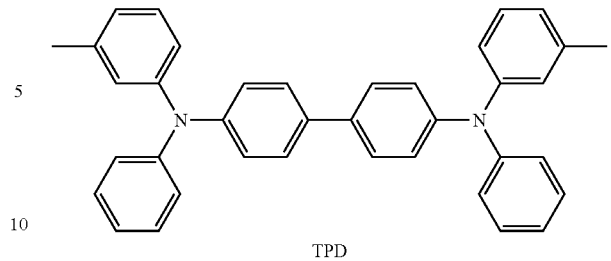

TPD

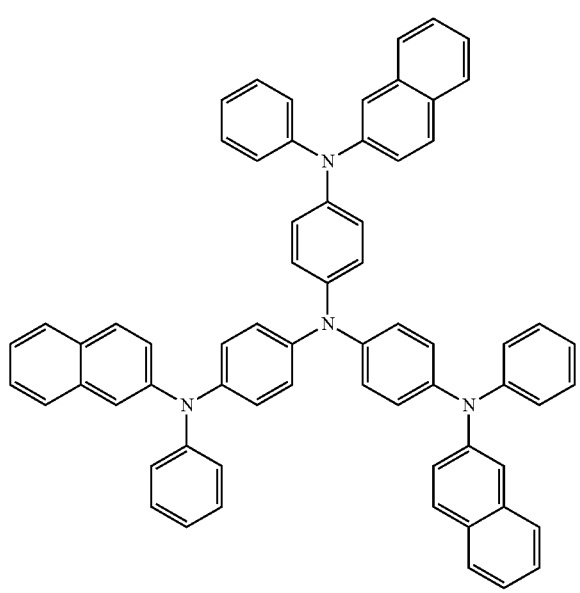

2-TNATA

NPB

The thickness of the HIL 13 may be about 100 to about 10000 Å, and for example, about 100 to about 1000 Å. When the thickness of the HIL 13 is within this range, the HIL 13 may have a satisfactory hole injecting ability without a substantial increase in driving voltage.

Then, a HTL 14 may be formed on the HIL 13 by vacuum deposition, a wet process, laser induced thermal imaging, or the like. When the HTL 14 is formed by vacuum deposition or spin coating, the conditions for deposition and coating may be similar to those for the formation of the HIL 13, although the conditions for the deposition and coating may vary according to the material that is used to form the HTL 14.

The HTL 14 may be formed of the condensed-cyclic compound as described above. Alternatively, the HTL 14 may be formed of known HTL materials, for example, TPD represented by the formula shown below, and NPB represented by the formula shown below:

The thickness of the HTL 14 may be in the range of about 50 to about 1,000 Å, for example, about 100 to about 800 Å. When the thickness of the HTL 14 is within this range, the HTL 14 may have an excellent hole transporting ability without a substantial increase in driving voltage.

Then, an EML 15 may be formed on the HTL 14 by vacuum deposition, a wet process, laser induced thermal imaging, or the like. When the EML 15 is formed using vacuum deposition or spin coating, the deposition and coating conditions may be similar to those for formation of the HIL 13, although the deposition and coating conditions may vary according to a compound that is used to form the EML 15.

The EML 15 may be the first layer including the condensed-cyclic compound represented by Formula 1 as described above. The EML 15 may further include a known phosphorescent host, fluorescent host, phosphorescent dopant, or fluorescent dopant in addition to the condensed-cyclic compound represented by Formula 1. The condensed-cyclic compound may function as the phosphorescent host, fluorescent host, phosphorescent dopant, or fluorescent dopant.

For example, examples of known hosts include 4,4'-N,N'-dicarbazole-biphenyl (CBP), 9,10-di-(naphthalene-2-yl)anthracene (ADN, represented by the formula shown below), TPBI represented by the formula shown below, TBADN represented by the formula shown below, and E3 represented by the formula shown below, but are not limited thereto:

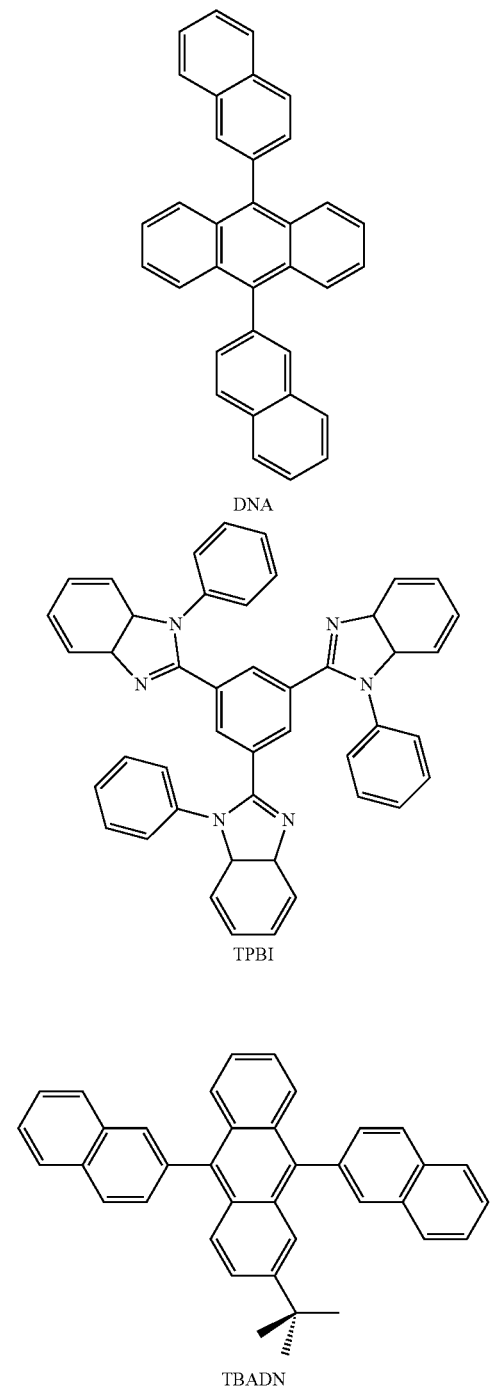

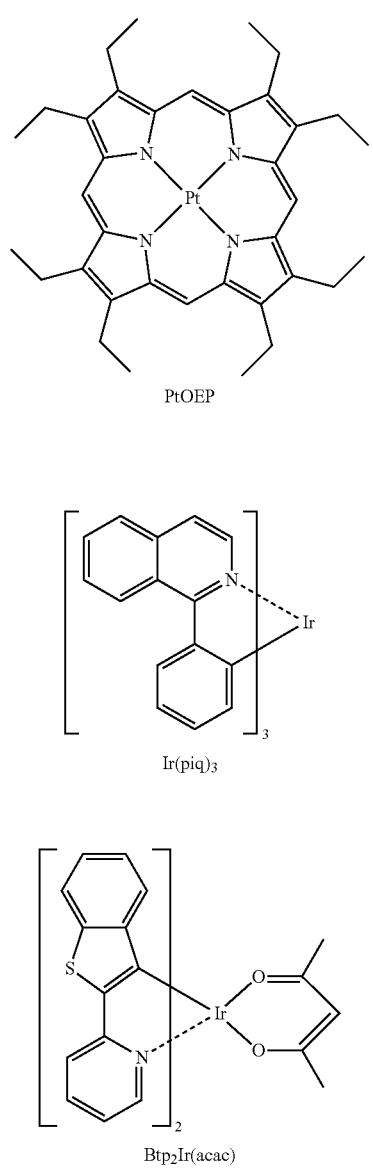

Meanwhile, examples of known dopants include PtOEP represented by the formula shown below, Ir(piq)$_3$ represented by the formula shown below, and Btp$_2$Ir(acac) represented by the formula shown below, but are not limited thereto:

Also, examples of known green dopants include Ir(ppy)$_3$ (ppy=phenylpyridine), Ir(ppy)$_2$(acac), represented by the formula shown below, and Ir(mpyp)$_3$ represented by the formula shown below, but are not limited thereto:

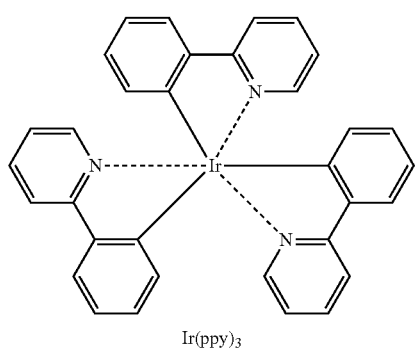

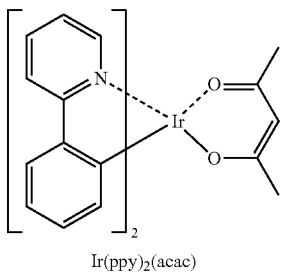

Ir(ppy)₂(acac)

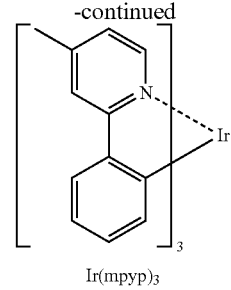

Ir(mpyp)₃

Examples of known blue dopants include F₂Irpic represented by the formula shown below, (F₂ppy)₂Ir(tmd) represented by the formula shown below, Ir(dfppz)₃ represented by the formula shown below, DPVBi represented by the formula shown below, 4,4'-bis(4-diphenylaminostyryl)biphenyl (DPAVBi, represented by the formula shown below), and 2,5,8,11-tetra-t-butyl pherylene (TBPe, represented by the formula shown below), but are not limited thereto:

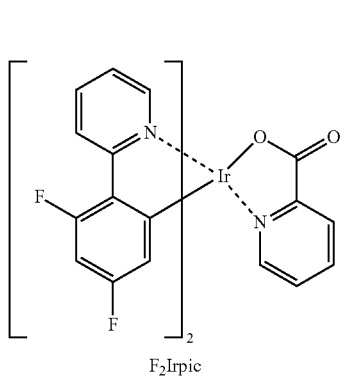

F₂Irpic

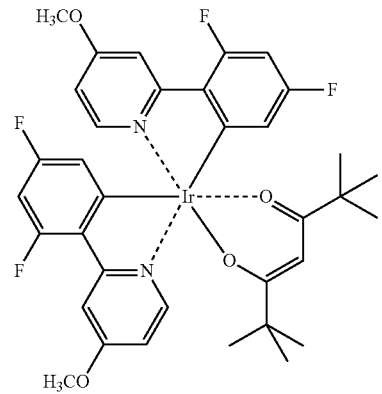

(F₂ppy)₂Ir(tmd)

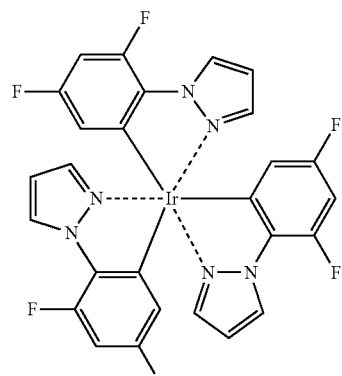

Ir(dfppz)₃

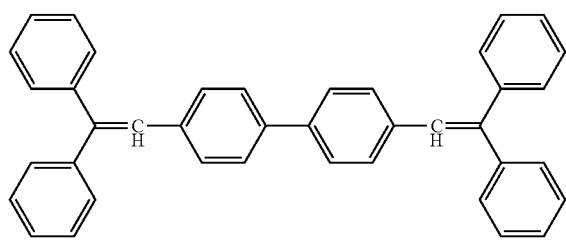

DPVBi

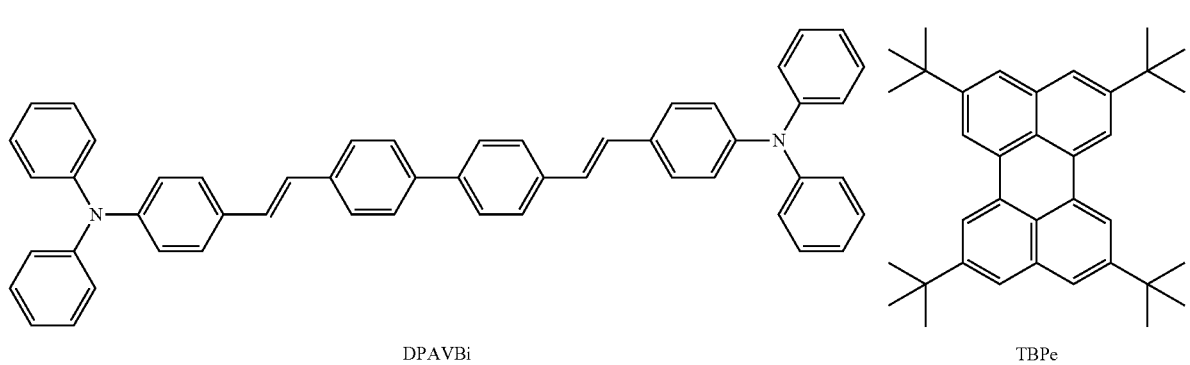

DPAVBi

TBPe

If the EML 15 includes the host and the dopant, the amount of the dopant may be in the range of about 0.01 to about 15 parts by weight based on 100 parts by weight of the host, but is not limited thereto.

The thickness of the EML 15 may be in the range of about 100 Å to about 1000 Å, for example, about 200 Å to about 600 Å. When the thickness of the EML 15 is within this range, the EML 15 may have an excellent light emitting ability without a substantial increase in driving voltage.

When a phosphorescent dopant is also used to form the EML 15, a HBL (not shown in FIG. 1) may be formed between the HTL 14 and the EML 15 by using vacuum deposition, a wet process, laser induced thermal imaging, or the like, in order to prevent diffusion of triplet excitons or holes into an ETL 16. When the HBL is formed using vacuum deposition or spin coating, the conditions for deposition and coating may be similar to those for the formation of the HIL 130, although the conditions for deposition and coating may vary according to the material that is used to form the HBL. Any material that is commonly used to form a HBL may be used. Examples of materials for forming the HBL include an oxadiazole derivative, a triazole derivative, and a phenanthroline derivative.

The thickness of the HBL may be in a range of about 50 to about 1,000 Å, for example, about 100 to about 300 Å. When the thickness of the HBL is within this range, the HBL may have an excellent hole blocking ability without a substantial increase in driving voltage.

Then, an ETL 16 is formed on the EML 15 (or HBL) using various methods, for example, by vacuum deposition, a wet process, laser induced thermal imaging, or the like. When the ETL 16 is formed using vacuum deposition or spin coating, the deposition and coating conditions may be similar to those for formation of the HIL 13, although the deposition and coating conditions may vary according to a compound that is used to form the ETL 16. A material that is used to form the ETL 16 may be a material that can stably transport electrons injected from the electron injecting electrode (cathode) and any known material may be used. Examples of the ETL material include, but are not limited to, quinoline derivatives, such as tris(8-quinolinolate)aluminum ($Alq_3$), TAZ represented by the formula shown below, and beryllium bis(benzoquinolin-10-olate) ($Balq_2$, represented by the formula shown below).

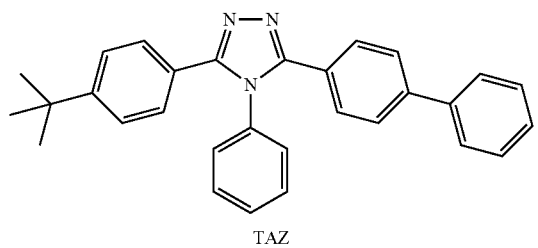

TAZ

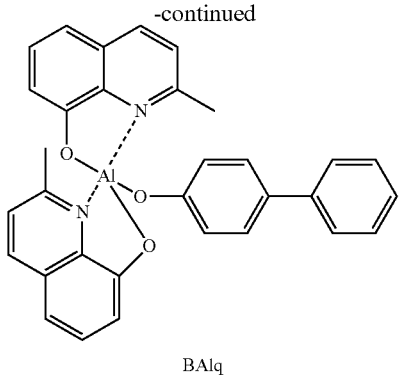

BAlq

The thickness of the ETL 16 may be in the range of about 100 Å to about 1000 Å, for example, about 150 Å to about 500 Å. When the thickness of the ETL 16 is within this range, the ETL 16 may have an excellent electron transporting ability without a substantial increase in driving voltage.

In addition, an EIL 17, which facilitates injection of electrons from the cathode, may be formed on the ETL 16. Examples of materials for forming the EIL 17 include LiF, NaCl, CsF, $Li_2O$, and BaO, which are known in the art. The conditions for deposition of the EIL 17 are similar to those for formation of the HIL 13, although the deposition conditions may vary according to a material that is used to form the EIL 17.

The thickness of the EIL 17 may be in the range of about 1 to about 100 Å, for example, in the range of about 3 to about 90 Å. When the thickness of the EIL 17 is within this range, the EIL 17 may have a satisfactory electron injecting ability without a substantial increase in driving voltage.

The second electrode 18 is disposed on the EIL 17. The second electrode 18 may be a cathode, which is an electron injecting electrode. A metal for forming the second electrode 18 may be a metal, an alloy, an electrically conductive compound, which have a low-work function, or a mixture thereof. In this regard, the second electrode 18 may be a transmissive electrode formed of lithium (Li), magnesium (Mg), aluminum (Al), aluminum (Al)-lithium (Li), calcium (Ca), magnesium (Mg)-indium (In), magnesium (Mg)-silver (Ag), or the like. Meanwhile, in order to manufacture a top-emission type OLED, a transparent electrode formed of ITO or IZO may be used.

The OLED may be used in a flat panel display device including a transistor. Thus, there is provided a flat panel display device including a transistor that includes a source, a drain, a gate, and an active layer and an OLED as described above, wherein one of the source and drain is electrically connected to the first electrode of the OLED. The active layer of the transistor may be an amorphous silicon layer, a crystalline silicon layer, an organic semiconductor layer, an oxide semiconductor layer, or the like.

Hereinafter, one or more embodiments of the present invention will be described in detail with reference to the following examples. These examples are not intended to limit the purpose and scope of the one or more embodiments of the present invention.

EXAMPLES

Synthesis Example 1

Synthesis of Compound 6

Compound 6 was synthesized through Reaction Scheme 1 below:

Reaction Scheme 1

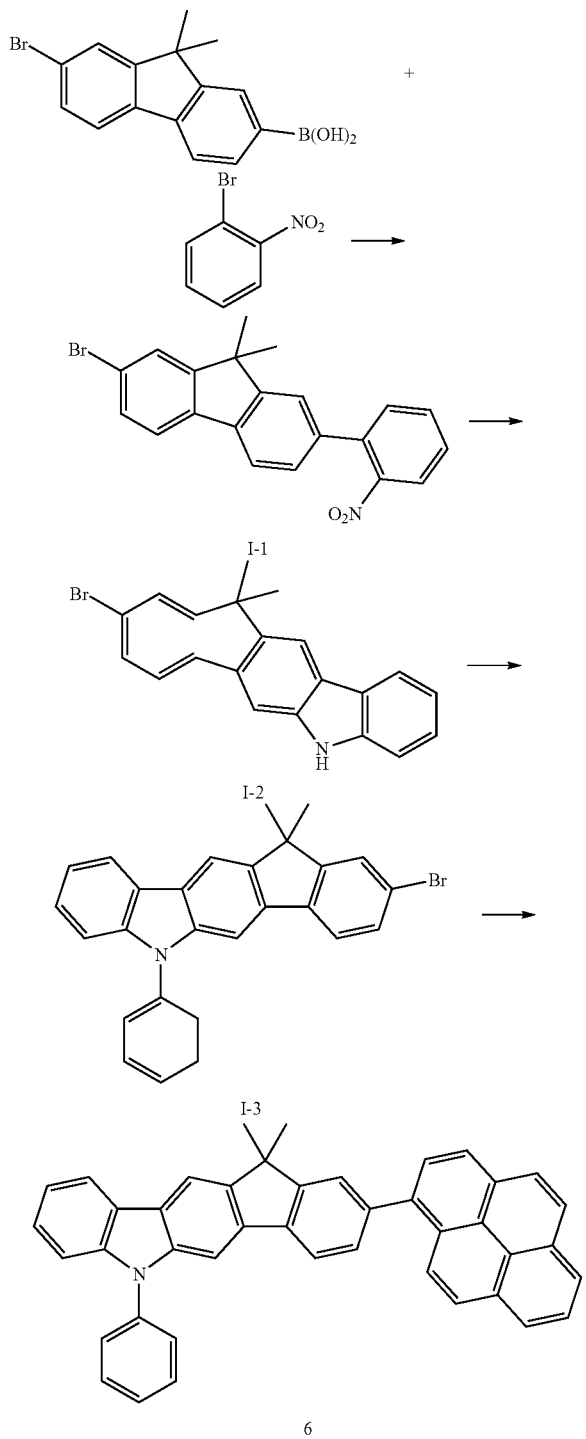

Synthesis of Intermediate I-1

6.34 g (20.0 mmol) of 2-bromo-9,9-dimethyl-7-fluoreneboraic acid, 4.04 g (20.0 mmol) of 2-bromonitrobenzene, 1.15 g (1.0 mmol) of Pd(PPh$_3$)$_4$, and 8.29 g (60.0 mmol) of K$_2$CO$_3$ were dissolved in 60 mL of a THF/H$_2$O (2/1) solution, and the mixture was stirred at 70° C. for 5 hours. The mixture was cooled to room temperature, 40 mL of water was added thereto, and the mixture was subjected to extraction three times with 50 mL of ethyl ether. An organic layer was collected and dried using magnesium sulfate to evaporate the solvent. The residue was separately purified using silica gel column chromatography to obtain 6.86 g of Intermediate I-1 (Yield: 87%). The produced compound was identified using liquid chromatography-mass spectrometry (LC-MS). C$_{21}$H$_{16}$BrNO$_2$: M+393.0.

Synthesis of Intermediate I-2

3.94 g (10.0 mmol) of Intermediate I-1 and 5.77 g (22 mmol) of triphenylphosphine (PPh$_3$) were dissolved in 30 mL of 1,2-dichlorobenzene, and the mixture was stirred at 170° C. for 12 hours. The mixture was cooled to room temperature, the solvent was removed in a vacuum, and the mixture was subjected to extraction three times with 50 mL of water and 50 mL of dichloromethane. An organic layer was collected and dried using magnesium sulfate to evaporate the solvent. The residue was separately purified using silica gel column chromatography to obtain 2.83 g of Intermediate I-2 (Yield: 78%) The produced compound was identified using LC-MS. C$_{21}$H$_{16}$BrN: M+361.0

Synthesis of Intermediate I-3

3.62 g (10.0 mmol) of Intermediate I-2, 3.06 g (15.0 mmol) of iodobenzene, 0.19 g (1.0 mmol) of CuI, 0.05 g (0.2 mmol) of 18-Crown-6, and 4.15 g (30.0 mmol) of K$_2$CO$_3$ were dissolved in 30 mL of 1,3-dimethyl-3,4,5,6-tetrahydro-2(1H)-pyrimidinone (DMPU), and the mixture was stirred at 170° C. for 12 hours. The mixture was cooled to room temperature and subjected to extraction three times with 50 mL of water and 50 mL of dichloromethane. An organic layer was collected and dried using magnesium sulfate to evaporate the solvent. The residue was separately purified using silica gel column chromatography to obtain 4.03 g of Intermediate I-3 (Yield: 92%). The produced compound was identified using LC-MS. C$_{27}$H$_{20}$BrN: M+437.1

Synthesis of Compound 6

2.19 g (5.0 mmol) of Intermediate I-3, 1.23 g (5.0 mmol) of 1-pyrene boraic acid, 0.29 g (0.25 mmol) of Pd(PPh$_3$)$_4$, and 2.07 g (15.0 mmol) of K$_2$CO$_3$ were dissolved in 30 mL of a THF/H$_2$O (2/1) solution, and the mixture was stirred at 70° C. for 5 hours. The mixture was is cooled to room temperature and subjected to extraction three times with 50 mL of water and 50 mL of dichloromethane. An organic layer was collected and dried using magnesium sulfate to evaporate the solvent. The residue was separately purified using silica gel column chromatography to obtain 2.18 g of Compound 6 (Yield: 78%). The produced compound was identified using LC-MS and nuclear magnetic resonance (NMR). C$_{43}$H$_{29}$N: M+559.2

$^1$H NMR (CDCl$_3$, 400 MHz) δ (ppm) 8.24 (d, 1H), 8.11-7.97 (m, 7H), 7.92-7.87 (m, 2H), 7.72 (d, 1H), 7.53 (s, 1H), 7.51-7.42 (m, 4H), 7.37-7.25 (m, 4H), 7.06 (d, 1H), 7.04-6.97 (m, 2H), 1.84 (s, 6H)

Synthesis Example 2

Synthesis of Compound 8

Compound 8 was synthesized through Reaction Scheme 2 below:

Reaction Scheme 2

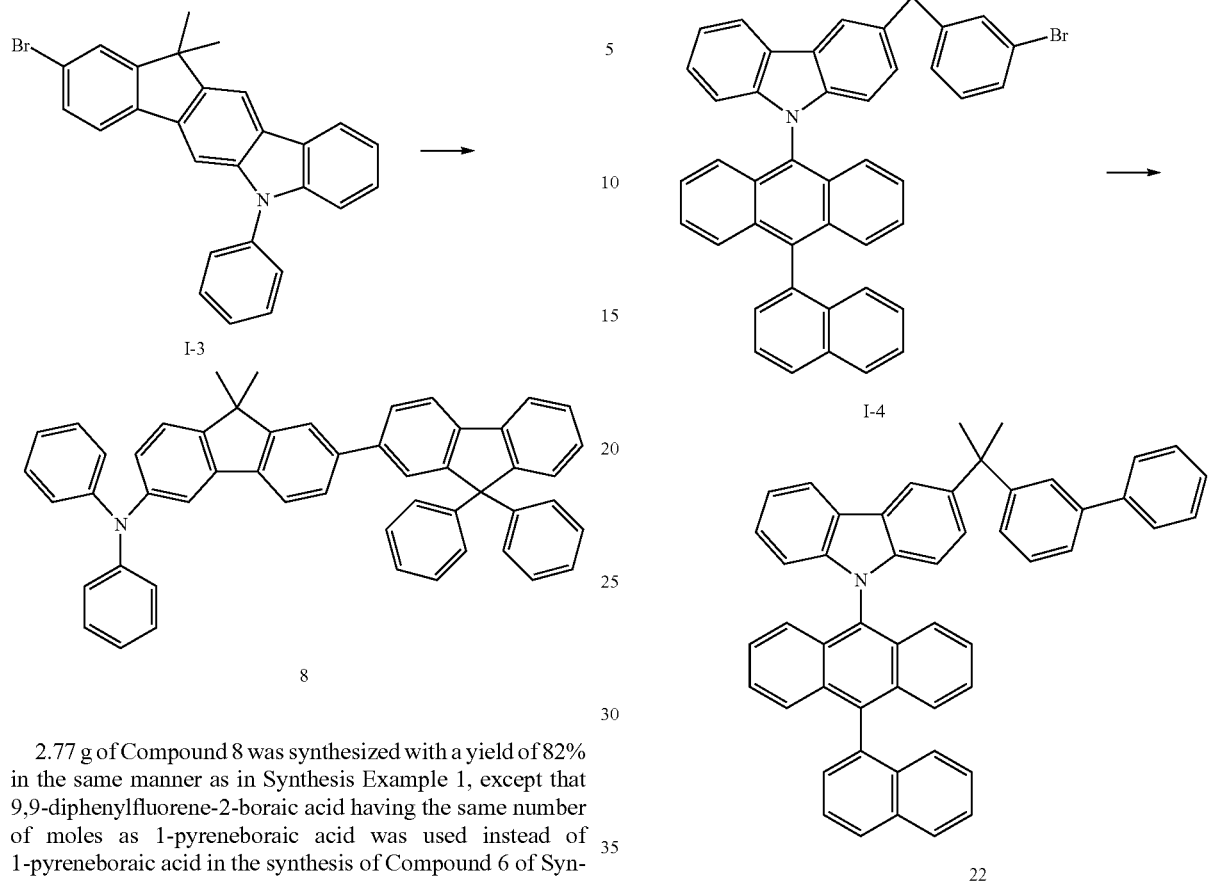

2.77 g of Compound 8 was synthesized with a yield of 82% in the same manner as in Synthesis Example 1, except that 9,9-diphenylfluorene-2-boraic acid having the same number of moles as 1-pyreneboraic acid was used instead of 1-pyreneboraic acid in the synthesis of Compound 6 of Synthesis Example 1. The produced compound was identified using LC-MS and NMR. $C_{52}H_{37}N$: M+675.3

$^1$H NMR (CDCl$_3$, 400 MHz) δ (ppm) 8.06-7.98 (m, 3H), 7.86 (dd, 1H), 7.52 (s, 1H), 7.51-7.41 (m, 8H), 7.37-7.25 (m, 6H), 7.21-7.16 (m, 4H), 7.09-6.97 (m, 5H), 6.96-6.89 (m, 3H), 1.85 (s, 6H)

Synthesis Example 3

Synthesis of Compound 22

Compound 22 was synthesized through Reaction Scheme 3 below:

Reaction Scheme 3

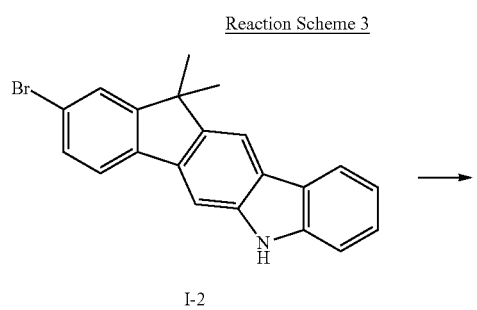

Synthesis of Intermediate I-4

5.25 g of Intermediate I-4 was synthesized with a yield of 79% in the same manner as the synthesis of Intermediate I-3 in Synthesis Example 1, except that 9-bromo-10-naphthalene-anthracene having the same number of moles as iodobenzene was used instead of iodobenzene in the synthesis of Intermediate I-3 of Synthesis Example 1. The produced compound was identified using LC-MS. $C_{45}H_{30}BrN$: M+663.2

Synthesis of Compound 22

2.94 g of Compound 22 was synthesized with a yield of 89% in the same manner as the synthesis of Compound 6 of Synthesis Example 1, except that Intermediate I-4 was used instead of Intermediate I-3 and 1-phenylboraic acid was used instead of 1-pyreneboraic acid in the synthesis of Compound 6 of Synthesis Example 1. The produced compound was identified using LC-MS and NMR. $C_{51}H_{35}N$: M+661.3

$^1$H NMR (CDCl$_3$, 400 MHz) δ (ppm) 8.68-8.62 (m, 2H), 8.13 (d, 1H), 8.04 (dt, 2H), 7.98-7.92 (m, 3H), 7.73 (dt, 2H), 7.64 (dt, 1H), 7.55-7.43 (m, 8H), 7.39-7.28 (m, 5H), 7.26-7.21 (m, 1H), 7.08 (d, 1H), 6.99-6.95 (m, 2H), 6.78 (dd, 1H), 1.84 (s, 6H)

Synthesis Example 4

Synthesis of Compound 27

Compound 27 was synthesized through Reaction Scheme 4 below:

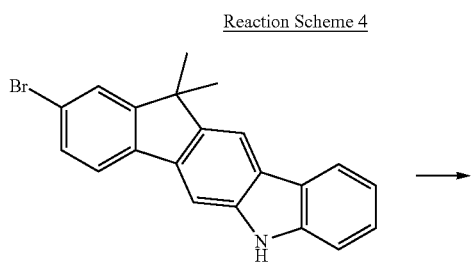

Reaction Scheme 4

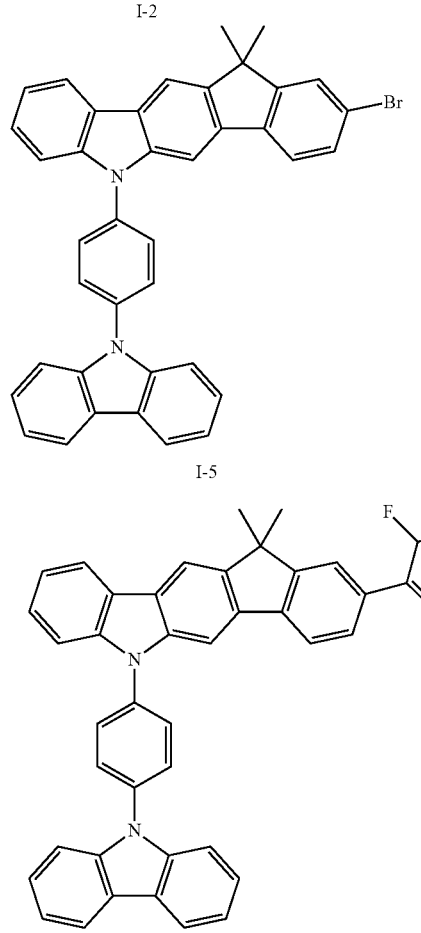

Synthesis of Intermediate I-5

2.44 g of Intermediate I-5 was synthesized with a yield of 81% in the same manner as the synthesis of Intermediate I-1 of Synthesis Example 1, except that 9-(4-bromophenyl)carbazole was used instead of iodobenzene in the synthesis of Intermediate I-3 of Synthesis Example 1. The produced compound was identified using LC-MS. $C_{39}H_{27}BrN_2$: M+602.1

Synthesis of Compound 27

2.31 g of Compound 27 was synthesized with a yield of 67% in the same manner as the synthesis of Compound 6 of Synthesis Example 1, except that Intermediate I-5 was used instead of Intermediate I-3 and 2,3,4,5,6-pentafluorophenyl-1-boraic acid was used instead of 1-pyreneboraic acid in the synthesis of Compound 6 of Synthesis Example 1. The produced compound was identified using LC-MS and NMR. $C_{45}H_{27}F_5N_2$: M+690.2

$^1$H NMR (CDCl$_3$, 400 MHz) δ (ppm) 8.09 (d, 2H), 8.05-8.02 (m, 1H), 7.98 (s, 1H), 7.78-7.69 (m, 4H), 7.51 (s, 1H), 7.37-7.30 (m, 6H), 7.28-7.20 (m, 3H), 7.11 (d, 1H), 6.96 (dd, 1H), 6.78 (d, 1H), 1.86 (s, 6H)

Synthesis Example 5

Synthesis of Compound 35

Compound 35 was synthesized through Reaction Scheme 5 below:

Reaction Scheme 5

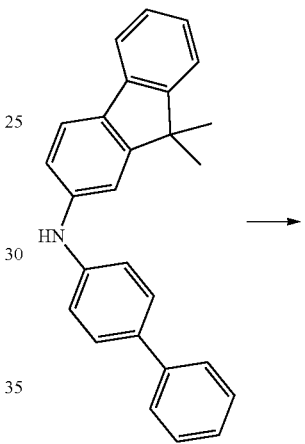

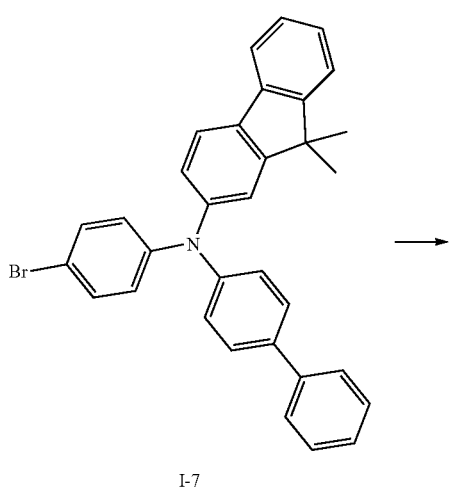

-continued

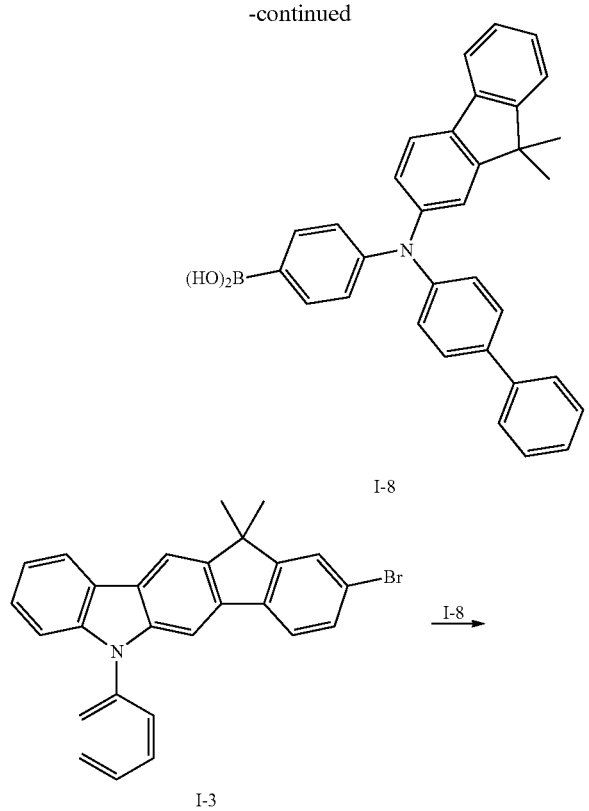

n-BuLi was slowly added thereto at −78° C. The mixture was stirred at the same temperature for 1 hour, 1.67 ml (15.0 mmol) of B(OMe)₃ was added thereto, and the mixture was stirred for 1 hour. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 3.32 g of Intermediate I-8 (Yield: 69%). The produced compound was identified using LC-MS. $C_{33}H_{28}BNO_2$: M+481.2

Synthesis of Compound 35

3.06 g of Compound 35 was synthesized with a yield of 77% in the same manner as the synthesis of Compound 6 of Synthesis Example 1, except that Intermediate I-8 was used instead of 1-pyreneborai acid in the synthesis of Compound 6 of Synthesis Example 1. The produced compound was identified using LC-MS and NMR. $C_{60}H_{46}N_2$: M+794.4

¹H NMR (CDCl₃, 400 MHz) δ (ppm) 8.06-8.02 (m, 1H), 7.99-7.96 (m, 2H), 7.76-7.72 (m, 2H), 7.69-7.57 (m, 6H), 7.51 (s, 1H), 7.49-7.43 (m, 3H), 7.40-7.21 (m, 9H), 7.17-7.07 (m, 4H), 6.95 (dt, 1H), 6.75-6.68 (m, 4H), 6.64 (dd, 1H), 1.86 (s, 6H), 1.84 (s, 6H)

Synthesis Example 6

Synthesis of Compound 44

Compound 44 was synthesized through Reaction Scheme 6 below:

Reaction Scheme 6

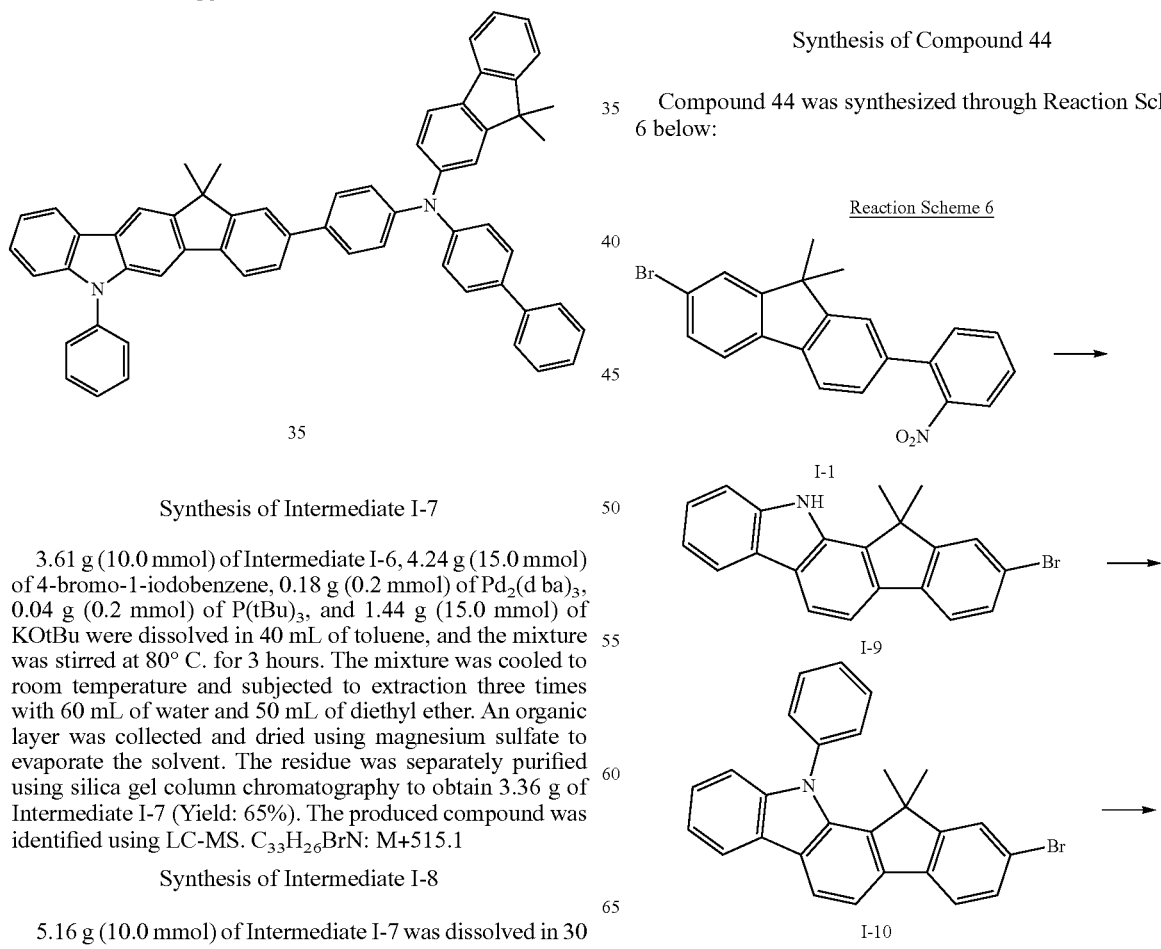

Synthesis of Intermediate I-7

3.61 g (10.0 mmol) of Intermediate I-6, 4.24 g (15.0 mmol) of 4-bromo-1-iodobenzene, 0.18 g (0.2 mmol) of Pd₂(d ba)₃, 0.04 g (0.2 mmol) of P(tBu)₃, and 1.44 g (15.0 mmol) of KOtBu were dissolved in 40 mL of toluene, and the mixture was stirred at 80° C. for 3 hours. The mixture was cooled to room temperature and subjected to extraction three times with 60 mL of water and 50 mL of diethyl ether. An organic layer was collected and dried using magnesium sulfate to evaporate the solvent. The residue was separately purified using silica gel column chromatography to obtain 3.36 g of Intermediate I-7 (Yield: 65%). The produced compound was identified using LC-MS. $C_{33}H_{26}BrN$: M+515.1

Synthesis of Intermediate I-8

5.16 g (10.0 mmol) of Intermediate I-7 was dissolved in 30 mL of THF, and 4.4 mL (11.0 mmol, 2.5M in Hexane) of

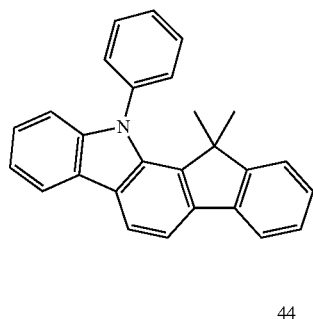

44

Synthesis of Intermediate I-9

3.94 g (10.0 mmol) of Intermediate I-1 and 5.77 g (22 mmol) of triphenylphosphine (PPh$_3$) were dissolved in 30 mL of 1,2-dichlorobenzene, and the mixture was stirred at 220° C. for 12 hours. The mixture was cooled to room temperature, the solvent was removed in a vacuum, and the mixture was subjected to extraction three times with 50 mL of water and 50 mL of dichloromethane. An organic layer was collected and dried using magnesium sulfate to evaporate the solvent. The residue was separately purified using silica gel column chromatography to obtain 3.04 g of Intermediate I-9 (Yield: 84%) The produced compound was identified using LC-MS. $C_{21}H_{16}BrN$: M+361.0

Synthesis of Intermediate I-10

4.08 g of Intermediate I-10 was synthesized with a yield of 93% in the same manner as the synthesis of Intermediate I-3, using Intermediate I-9. The produced compound was identified using LC-MS. $C_{27}H_{20}BrN$: M+437.1

Synthesis of Compound 44

2.61 g of Compound 44 was synthesized with a yield of 79% in the same manner as the synthesis of Compound 6 of Synthesis Example 1, except that Intermediate I-10 was used instead of Intermediate I-3 and 9-(10-naphthalenyl)-anthraceneboraic acid was used instead of 1-pyreneboraic acid in the synthesis of Compound 6 of Synthesis Example 1. The produced compound was identified using LC-MS and NMR. $C_{51}H_{35}N$: M+661.3

$^1$H NMR (CDCl$_3$, 400 MHz) δ (ppm) 8.13 (d, 1H), 8.07-8.02 (m, 2H), 7.97 (d, 1H), 7.89 (d, 1H), 7.74-7.62 (m, 7H), 7.49-7.42 (m, 5H), 7.39-7.25 (m, 9H), 7.05-7.00 (m, 2H), 6.97 (d, 1H), 2.01 (s, 6H)

Synthesis Example 7

Synthesis of Compound 52

Compound 52 was synthesized through Reaction Scheme 7 below:

Reaction Scheme 7

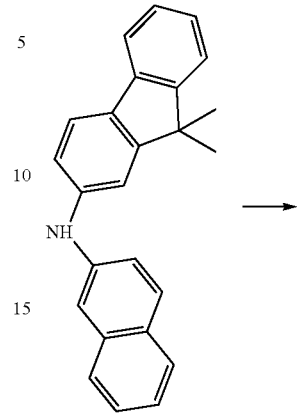

I-11

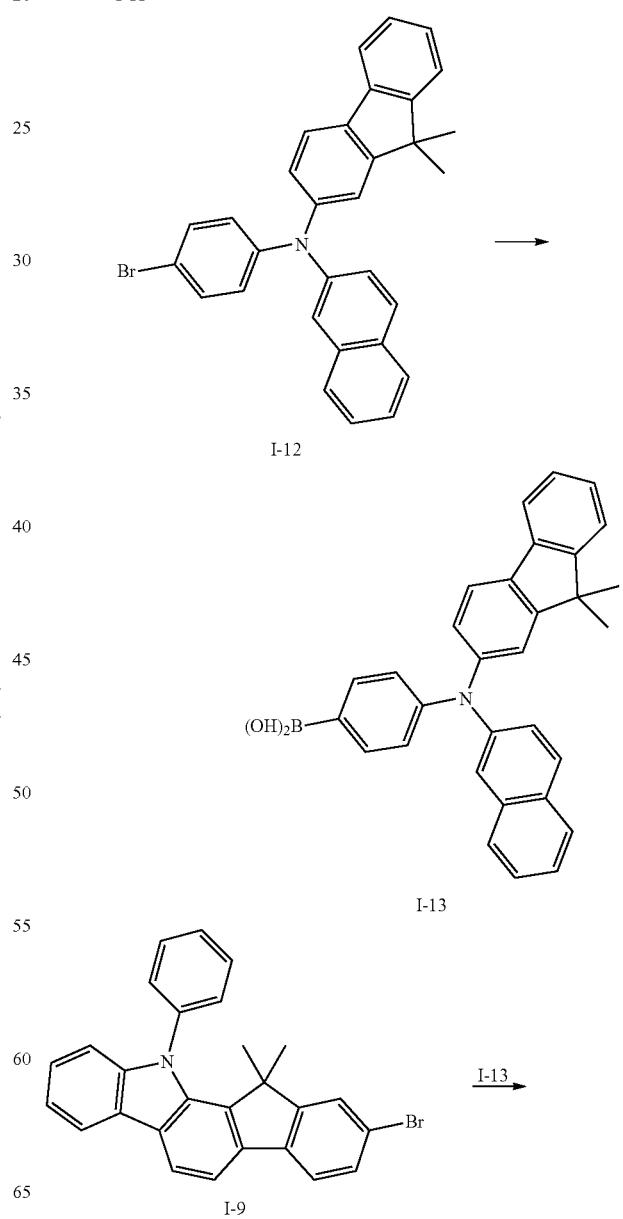

I-12

I-13

I-9

-continued

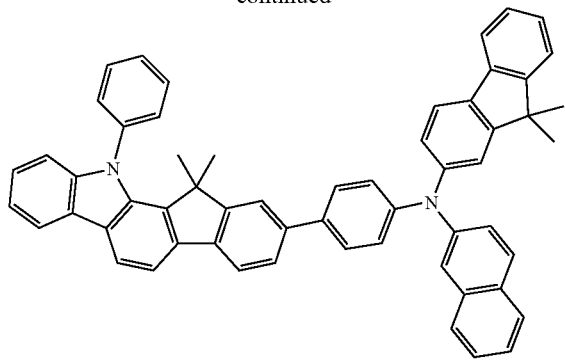

52

Synthesis of Intermediate I-12

3.33 g of Intermediate I-12 was synthesized with a yield of 68% in the same manner as the synthesis of Intermediate I-7, using Intermediate I-11 and 4-bromo-1-iodobenzene. The produced compound was identified using LC-MS. $C_{31}H_{24}BrN$: M+489.1

Synthesis of Intermediate I-13

3.46 g of Intermediate I-13 was synthesized with a yield of 76% in the same manner as the synthesis of Intermediate I-8, using Intermediate I-12. The produced compound was identified using LC-MS. $C_{31}H_{26}BNO_2$: M+455.2

Synthesis of Compound 52

3.19 g of Compound 52 was synthesized with a yield of 83% in the same manner as the synthesis of Compound 6 of Synthesis Example 1, except that Intermediate I-9 was used instead of Intermediate I-3 and Intermediate I-13 was used instead of 1-pyreneboraic acid in the synthesis of Compound 6 of Synthesis Example 1. The produced compound was identified using LC-MS and NMR. $C_{58}H_{44}N_2$: M+768.4

$^1$H NMR (CDCl$_3$, 400 MHz) δ (ppm) 8.06-8.03 (m, 1H), 7.99-7.95 (m, 2H), 7.91-7.85 (m, 2H), 7.70-7.54 (m, 7H), 7.49-7.42 (m, 5H), 7.37-7.28 (m, 5H), 7.22 (dt, 1H), 7.16-7.06 (m, 5H), 6.95 (dt, 1H), 6.72-6.67 (m, 2H), 6.63 (dd, 1H), 2.03 (s, 6H), 1.85 (s, 6H)

Example 1

A 15 Ω/cm$^2$ (1200 Å) ITO glass substrate (available from Corning Co.) was cut to a size of 50 mm×50 mm×0.7 mm, ultrasonically washed with isopropyl alcohol for 5 minutes and then with pure water for 5 minutes, and washed again with UV ozone for 30 minutes. The prepared ITO glass substrate was installed in a vacuum deposition apparatus. Then, 2-TNATA was vacuum deposited on the ITO glass substrate to form a HIL having a thickness of 600 Å, and then NPB was vacuum deposited on the HIL to form a HTL having a thickness of 300 Å. Compound 6 as a host and DPVBi as a dopant were deposited on the HTL at the same time in a weight ratio of 98:2 to form an EML with a thickness of 300 Å. Alq3 was vacuum-deposited on the EML to form an ETL with a thickness of 300 Å. LiF was vacuum-deposited on the ETL to form an EIL with a thickness of 10 Å and Al was vacuum-deposited on the EIL to form a cathode with a thickness of 3000 Å, thereby completing the manufacture of an OLED.

Example 2

An OLED was manufactured in the same manner as in Example 1, except that Compound 8 was used instead of Compound 6 as the host when the EML was formed.

Example 3

An OLED was manufactured in the same manner as in Example 1, except that Compound 22 was used instead of Compound 6 as the host when the EML was formed.

Example 4

An OLED was manufactured in the same manner as in Example 1, except that Compound 27 was used instead of Compound 6 as the host when the EML was formed.

Example 5

An OLED was manufactured in the same manner as in Example 1, except that Compound 44 was used instead of Compound 6 as the host when the EML was formed.

Example 6

An OLED was manufactured in the same manner as in Example 1, except that ADN was used instead of Compound 6 as the host and Compound 35 was used instead of DPVBi as the dopant when the EML was formed.

Example 7

An OLED was manufactured in the same manner as in Example 6, except that Compound 52 was used instead of Compound 35 as the dopant when the EML was formed.

Comparative Example 1

An OLED was manufactured in the same manner as in Example 1, except that ADN was used instead of Compound 6 as the host when the EML was formed.

Evaluation Example

Driving voltage, current density, brightness, efficiency, and half lifespan of the organic light emitting diodes manufactured according to Examples 1 to 7 and Comparative Example 1 were evaluated using PR650 Spectroscan Source Measurement Unit (PhotoReaserch). The results are shown in Table 1 below:

TABLE 1

| | EML | | Driving voltage | Current density | Brightness | Efficiency | | Half lifespan |
|---|---|---|---|---|---|---|---|---|
| | Host | Dopant | (V) | $(mA/cm^2)^2$ | $(Cd/m^2)$ | (Cd/A) | Color | (hr @100 $mA/cm^2$) |
| Example 1 | Compound 6 | DPVBi | 6.62 | 50 | 1,975 | 3.95 | blue | 185 |
| Example 2 | Compound 8 | DPVBi | 6.58 | 50 | 2,265 | 4.53 | blue | 198 |
| Example 3 | Compound 22 | DPVBi | 6.49 | 50 | 2,876 | 5.75 | blue | 231 |
| Example 4 | Compound 27 | DPVBi | 6.13 | 50 | 2,158 | 4.32 | blue | 189 |
| Example 5 | Compound 44 | DPVBi | 6.54 | 50 | 2,915 | 5.83 | blue | 260 |
| Example 6 | ADN | Compound 35 | 6.51 | 50 | 3,425 | 6.85 | blue | 226 |
| Example 7 | ADN | Compound 52 | 6.45 | 50 | 3,348 | 6.69 | blue | 267 |
| Comparative Example 1 | ADN | DPVBi | 7.85 | 50 | 1,560 | 3.12 | blue | 113 |

Referring to Table 1, it was identified that the OLEDs manufactured according to Examples 1 to 7 had better characteristics than the OLED manufactured according to Comparative Example 1.

The OLED including the condensed-cyclic compound represented by Formula 1 has excellent characteristics, for example, high efficiency and long lifespan, and thus a flat panel display device with excellent characteristics may be manufactured.

While the present invention has been particularly shown and described with reference to exemplary embodiments thereof, it will be understood by those of ordinary skill in the art that various changes in form and details may be made therein without departing from the spirit and scope of the present invention as defined by the following claims.

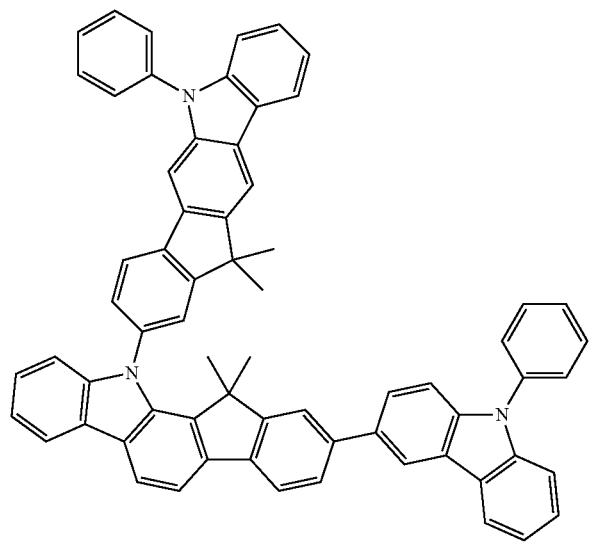
63
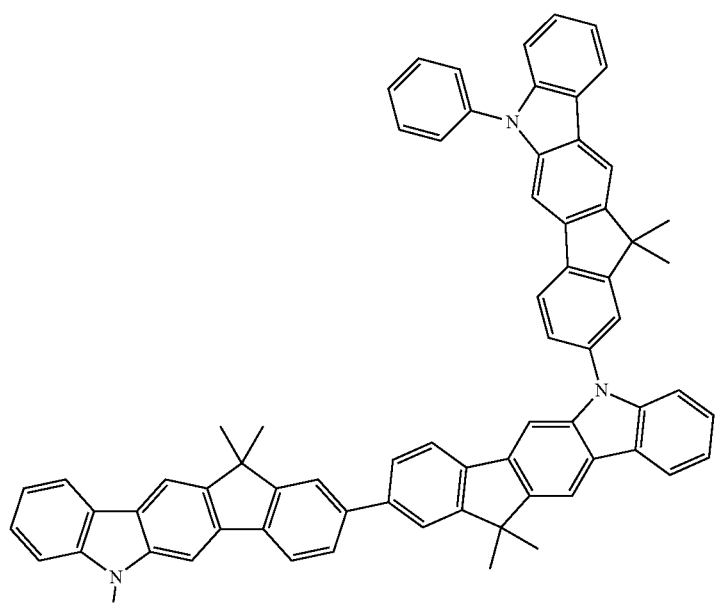
64
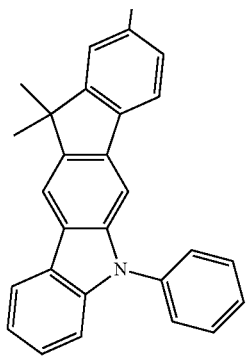

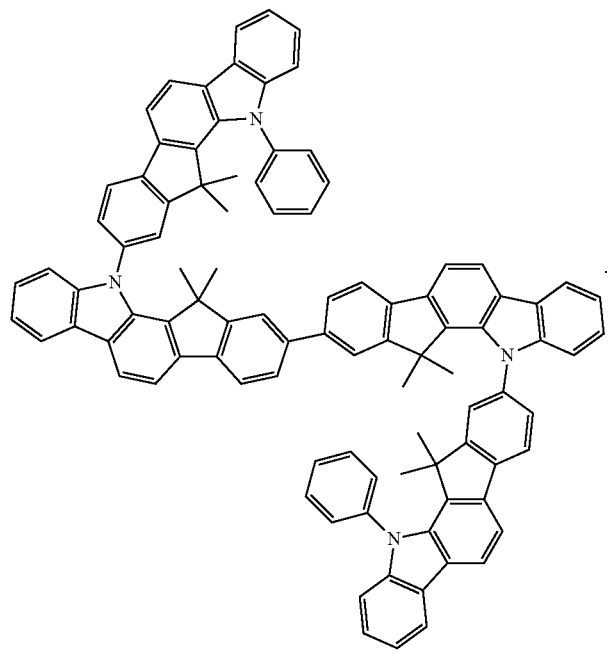

What is claimed:

1. A condensed-cyclic compound represented by Formula 1 below:

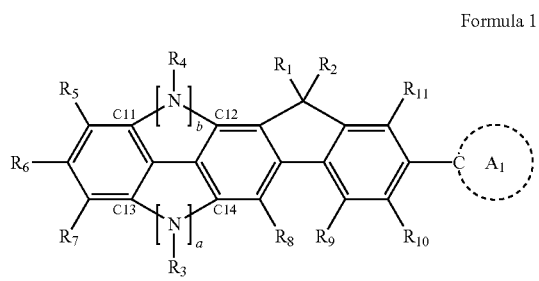

Formula 1 wherein either a=1 and b=0, or a=0 and b=1;

when a=1, b=0, —$R_{12}$ is connected to $C_{11}$, and $R_{13}$ is connected to $C_{12}$, and when a=0, b=1, —$R_{12}$ is connected to $C_{13}$, and $R_{13}$ is connected to $C_{14}$;

$A_1$ is a $C_6$-$C_{60}$ aryl group substituted with at least —N($Q_{11}$)($Q_{12}$), a $C_2$-$C_{60}$ heterocyclic group substituted with at least —N($Q_{11}$)($Q_{12}$), a group represented by Formula 2A below, or a group represented by Formula 2B below:

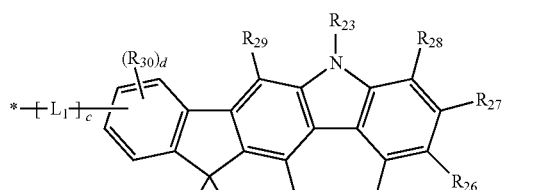

Formula 2A

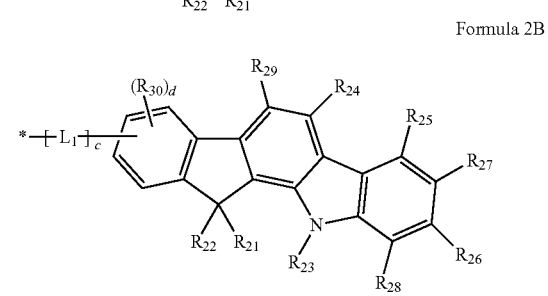

Formula 2B $L_1$ is a substituted or unsubstituted $C_6$-$C_{60}$ arylene group;
c is an integer from 0 to 5;
d is an integer from 1 to 4;
$R_1$, $R_2$, and $R_{21}$ to $R_{30}$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heterocyclic group, —N($Q_1$)($Q_2$), —Si($Q_3$)($Q_4$)($Q_5$), a group represented by Formula 3A below, or a group represented by Formula 3B below;

$R_5$ to $R_{13}$ are a hydrogen atom,
$R_3$ and $R_4$ are each independently
a $C_3$-$C_{60}$ cycloalkyl group;
a $C_3$-$C_{60}$ cycloalkyl group substituted with at least one of a heavy hydrogen atom, a halogen atom, a hydroxyl group, a cyano group, a methyl group, an ethyl group, a propyl group, a butyl group, a pentyl group, a methoxy group, an ethoxy group, a propoxy group, a pentoxy group, a phenyl group, a naphthyl group, and an anthryl group;

a $C_3$-$C_{60}$ cycloalkenyl group;
a $C_3$-$C_{60}$ cycloalkenyl group substituted with at least one of a heavy hydrogen atom, a halogen atom, a hydroxyl group, a cyano group, a methyl group, an ethyl group, a propyl group, a butyl group, a pentyl group, a methoxy group, an ethoxy group, a propoxy group, a pentoxy group, a phenyl group, a naphthyl group, and an anthryl group;
a $C_6$-$C_{60}$ aryl group;
a $C_6$-$C_{60}$ aryl group substituted with at least one of a heavy hydrogen atom, a halogen atom, a hydroxyl group, a cyano group, a methyl group, an ethyl group, a propyl group, a butyl group, a pentyl group, a methoxy group, an ethoxy group, a propoxy group, a pentoxy group, a phenyl group, a naphthyl group, and an anthryl group;
a $C_2$-$C_{60}$ heterocyclic group;
a $C_2$-$C_{60}$ heterocyclic group substituted with at least one of a heavy hydrogen atom, a halogen atom, a hydroxyl group, a cyano group, a methyl group, an ethyl group, a propyl group, a butyl group, a pentyl group, a methoxy group, an ethoxy group, a propoxy group, a pentoxy group, a phenyl group, a naphthyl group, and an anthryl group;
a group represented by Formula 3A below; or
a group represented by Formula 3B below,

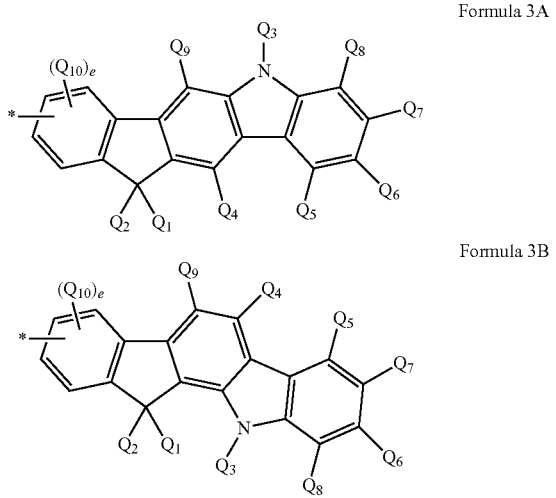

Formula 3A

Formula 3B $Q_1$ to $Q_{12}$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heterocyclic group; and
e is an integer from 1 to 4.

2. The condensed-cyclic compound of claim 1, wherein A1 is a phenyl group substituted with at least —$N(Q_{11})(Q_{12})$, a pentalenyl group substituted with at least —$N(Q_{11})(Q_{12})$, a indenyl group substituted with at least —$N(Q_{11})(Q_{12})$, a naphthyl group substituted with at least —$N(Q_{11})(Q_{12})$, a azulenyl group substituted with at least —$N(Q_{11})(Q_{12})$, a heptalenyl group substituted with at least —$N(Q_{11})(Q_{12})$, a indacenyl group substituted with at least —$N(Q_{11})(Q_{12})$, a acenaphtyl group substituted with at least —$N(Q_{11})(Q_{12})$, a fluorenyl group substituted with at least —$N(Q_{11})(Q_{12})$, a spiro-fluorenyl group substituted with at least —$N(Q_{11})(Q_{12})$, a phenalenyl group substituted with at least —$N(Q_{11})(Q_{12})$, a phenanthrenyl group substituted with at least —$N(Q_{11})(Q_{12})$, a anthryl group substituted with at least —$N(Q_{11})(Q_{12})$, a fluoranthenyl group substituted with at least —$N(Q_{11})(Q_{12})$, a triphenylenyl group substituted with at least —$N(Q_{11})(Q_{12})$, a pyrenyl group substituted with at least —$N(Q_{11})(Q_{12})$, a chrysenyl group substituted with at least —$N(Q_{11})(Q_{12})$, a naphthacenyl group substituted with at least —$N(Q_{11})(Q_{12})$, a picenyl group substituted with at least —$N(Q_{11})(Q_{12})$, a perylenyl group substituted with at least —$N(Q_{11})(Q_{12})$, a pentaphenyl group substituted with at least —$N(Q_{11})(Q_{12})$, a hexacenyl group substituted with at least —$N(Q_{11})(Q_{12})$, a pyrrolyl group substituted with at least —$N(Q_{11})(Q_{12})$, a imidazolyl group substituted with at least —$N(Q_{11})(Q_{12})$, a pyrazolyl group substituted with at least —$N(Q_{11})(Q_{12})$, a pyridinyl group substituted with at least —$N(Q_{11})(Q_{12})$, a pyrazinyl group substituted with at least —$N(Q_{11})(Q_{12})$, a pyrimidinyl group substituted with at least —$N(Q_{11})(Q_{12})$, a pyridazinyl group substituted with at least —$N(Q_{11})(Q_{12})$, a isoindolyl group substituted with at least —$N(Q_{11})(Q_{12})$, a indolyl group substituted with at least —$N(Q_{11})(Q_{12})$, a indazolyl group substituted with at least —$N(Q_{11})(Q_{12})$, a purinyl group substituted with at least —$N(Q_{11})(Q_{12})$, a quinolinyl group substituted with at least —$N(Q_{11})(Q_{12})$, a benzoquinolinyl group substituted with at least —$N(Q_{11})(Q_{12})$, a phthalazinyl group substituted with at least —$N(Q_{11})(Q_{12})$, a naphthyridinyl group substituted with at least —$N(Q_{11})(Q_{12})$, a quinoxalinyl group-substituted with at least —$N(Q_{11})(Q_{12})$, a quinazolinyl group substituted with at least —$N(Q_{11})(Q_{12})$, a cinnolinyl group substituted with at least —$N(Q_{11})(Q_{12})$, a carbazolyl group substituted with at least —$N(Q_{11})(Q_{12})$, a phenanthridinyl group substituted with at least —$N(Q_{11})(Q_{12})$, a acridinyl group substituted with at least —$N(Q_{11})(Q_{12})$, a phenanthrolinyl group substituted with at least —$N(Q_{11})(Q_{12})$, a phenazinyl group substituted with at least —$N(Q_{11})(Q_{12})$, a benzooxazolyl group substituted with at least —$N(Q_{11})(Q_{12})$, a benzoimidazolyl group substituted with at least —$N(Q_{11})(Q_{12})$, a furanyl group substituted with at least —$N(Q_{11})(Q_{12})$, a benzofuranyl group substituted with at least —$N(Q_{11})(Q_{12})$, a thiophenyl group substituted with at least —$N(Q_{11})(Q_{12})$, a benzothiophenyl group substituted with at least —$N(Q_{11})(Q_{12})$, a thiazolyl group substituted with at least —$N(Q_{11})(Q_{12})$, a isothiazolyl group substituted with at least —$N(Q_{11})(Q_{12})$, a benzothiazolyl group substituted with at least —$N(Q_{11})(Q_{12})$, a isoxazolyl group substituted with at least —$N(Q_{11})(Q_{12})$, a oxazolyl group substituted with at least —$N(Q_{11})(Q_{12})$, a triazolyl group substituted with at least —$N(Q_{11})(Q_{12})$, a tetrazolyl group substituted with at least —$N(Q_{11})(Q_{12})$, a oxadiazolyl group substituted with at least —$N(Q_{11})(Q_{12})$, a triazinyl group substituted with at least —$N(Q_{11})(Q_{12})$, a dibenzopuranyl group substituted with at least —$N(Q_{11})(Q_{12})$, or a dibenzothiophenyl group substituted with at least —$N(Q_{11})(Q_{12})$.

3. The condensed-cyclic compound of claim 1, wherein A1 is a phenyl group substituted with at least —$N(Q_{11})(Q_{12})$, a naphthyl group substituted with at least —$N(Q_{11})(Q_{12})$, a fluorenyl group substituted with at least —$N(Q_{11})(Q_{12})$, a spiro-fluorenyl group substituted with at least —$N(Q_{11})(Q_{12})$, a phenanthrenyl group substituted with at least —$N(Q_{11})(Q_{12})$, a anthryl group substituted with at least —N(Q₁₁)(Q₁₂), a triphenylenyl group substituted with at least —N(Q₁₁)(Q₁₂), a pyrenyl group substituted with at least —N(Q₁₁)(Q₁₂), a carbazolyl group substituted with at least —N(Q₁₁)(Q₁₂), a benzoimidazolyl group substituted with at least —N(Q₁₁)(Q₁₂), a triazinyl group substituted with at least —N(Q₁₁)(Q₁₂), a dibenzopuranyl group substituted with at least —N(Q₁₁)(Q₁₂), a dibenzothiophenyl group substituted with at least —N(Q₁₁)(Q₁₂), or oxadiazolyl group substituted with at least —N(Q₁₁)(Q₁₂).

4. The condensed-cyclic compound of claim 1, wherein $A_1$ is selected from the group consisting of compounds represented by Formulae 5A to 5P below:

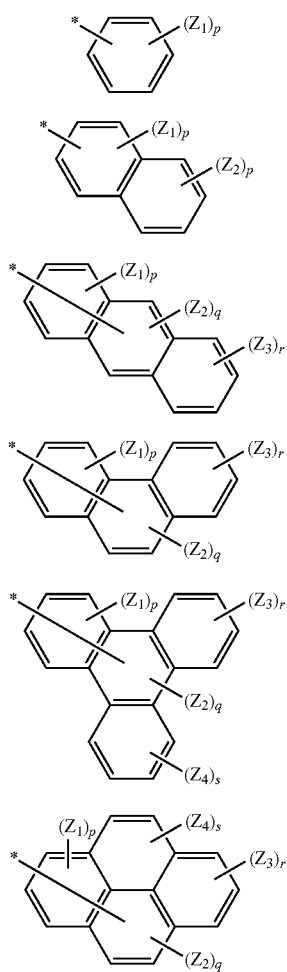

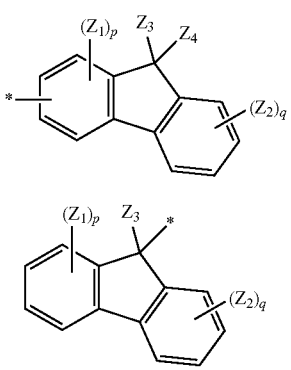

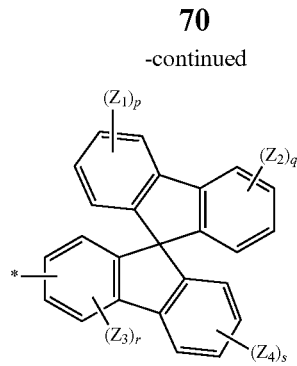

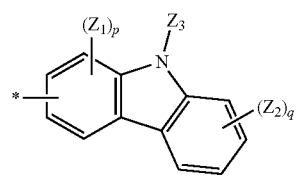

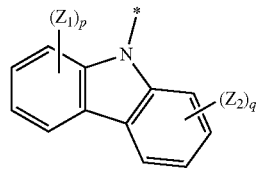

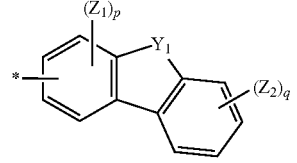

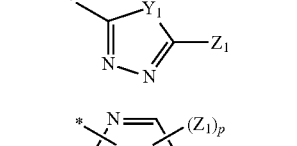

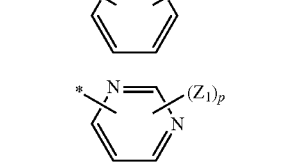

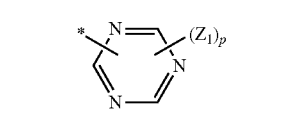

wherein p, q, r and s are each independently an integer from 1 to 4;

$Y_1$ is O or S;

$Z_1$ to $Z_4$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ hetero cyclic group, —N($Q_{11}$)($Q_{12}$), or —Si($Q_{13}$)($Q_{14}$)($Q_{15}$);

$Q_{11}$ to $Q_{15}$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ hetero cyclic group; and Formulae 5A to 5P has at least —N($Q_{11}$)($Q_{12}$) as a substituent.

5. The condensed-cyclic compound of claim 4, wherein $Z_1$ to $Z_4$ are each independently a hydrogen atom, a heavy hydrogen atom, —F, a hydroxyl group, a cyano group, a nitro group, a carboxyl group, a substituted or unsubstituted $C_1$-$C_{10}$ alkyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted carbazolyl group, a substituted or unsubstituted benzoimidazolyl group, a substituted or unsubstituted triazinyl group, a substituted or unsubstituted dibenzopuranyl group, a substituted or unsubstituted dibenzothiophenyl group, a substituted or unsubstituted oxadiazolyl group, a substituted or unsubstituted imidazopyridinyl group, or —N($Q_{11}$)($Q_{12}$); and $Q_{11}$ to $Q_{12}$ are each independently a hydrogen atom, a heavy hydrogen atom, a halogen atom, a hydroxyl group, a cyano group, a nitro group, a carboxyl group, a substituted or unsubstituted $C_1$-$C_{10}$ alkyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted carbazolyl group, a substituted or unsubstituted benzoimidazolyl group, a substituted or unsubstituted triazinyl group, a substituted or unsubstituted dibenzopuranyl group, a substituted or unsubstituted dibenzothiophenyl group, a substituted or unsubstituted oxadiazolyl group, or a substituted or unsubstituted imidazopyridinyl group.

6. The condensed-cyclic compound of claim 1, wherein $A_1$ is a group represented by Formula 2A-1 below or a group represented by Formula 2B-1 below:

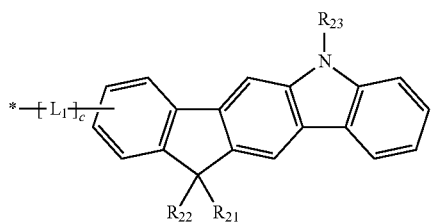

Formula 2A-1

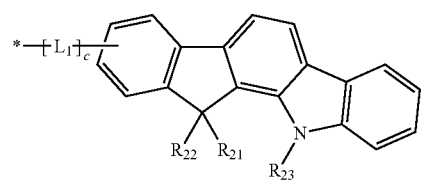

Formula 2B-1

$L_1$ is a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted spirofluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrycenylene group, a substituted or unsubstituted naphthacenylene group, a substituted or unsubstituted pycenylene group, a substituted or unsubstituted perylenylene group, a substituted or unsubstituted pentaphenylene group, or a substituted or unsubstituted hexacenylene group;

c is 0, 1 or 2;

$R_{21}$ to $R_{23}$ are each independently a hydrogen atom, a heavy hydrogen atom, a halogen atom, a hydroxyl group, a cyano group, a nitro group, a carboxyl group, a $C_1$-$C_{10}$ alkyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted dibenzofuranyl group, or a substituted or unsubstituted dibenzothiophenyl group, $-N(Q_1)(Q_2)$, a group represented by Formula 3A-1 below, or a group represented by Formula 3B-1 below; and

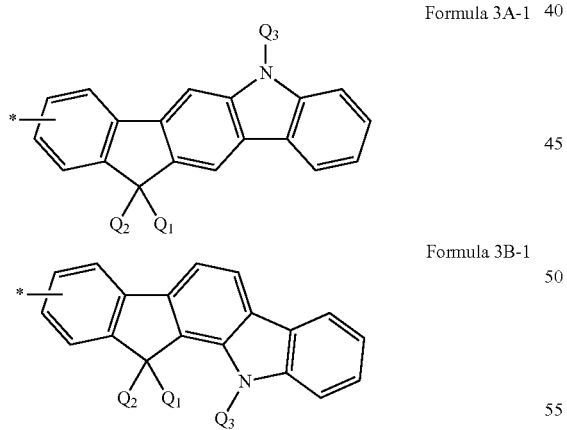

Formula 3A-1

Formula 3B-1

$Q_1$ to $Q_3$ are each independently a hydrogen atom, a heavy hydrogen atom, a halogen atom, a hydroxyl group, a cyano group, a nitro group, a carboxyl group, a $C_1$-$C_{10}$ alkyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted dibenzofuranyl group, or a substituted or unsubstituted dibenzothiophenyl group.

7. The condensed-cyclic compound of claim 6, wherein $L_1$ is a phenylene group;

c is 0 or 1;

$R_{21}$ and $R_{22}$ are each independently a hydrogen atom, a heavy hydrogen atom, a halogen atom, a hydroxyl group, a cyano group, a nitro group, a carboxyl group, a methyl group, an ethyl group, a propyl group, a butyl group, a pentyl group, a phenyl group, a naphthyl group, or an anthryl group;

$R_{23}$ is a hydrogen atom, a heavy hydrogen atom, a halogen atom, a hydroxyl group, a cyano group, a nitro group, a carboxyl group, a methyl group, an ethyl group, a propyl group, a butyl group, a pentyl group, a phenyl group, a naphthyl group, an anthryl group, the group represented by Formula 3A-1, or the group represented by Formula 3B-1; and in Formulae 3A-1 and 3B-1, $Q_1$ to $Q_3$ are each independently a hydrogen atom, a heavy hydrogen atom, a halogen atom, a hydroxyl group, a cyano group, a nitro group, a carboxyl group, a methyl group, an ethyl group, a propyl group, a butyl group, a pentyl group, a phenyl group, a naphthyl group, or an anthryl group.

8. The condensed-cyclic compound of claim 1, wherein $R_1$ and $R_2$ are each independently a hydrogen atom, a heavy hydrogen atom, a halogen atom, a hydroxyl group, a cyano group, a nitro group, a carboxyl group, a $C_1$-$C_{10}$ alkyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted dibenzofuranyl group, or a substituted or unsubstituted dibenzothiophenyl group, —N($Q_1$)($Q_2$), a group represented by Formula 3A-1 below, or a group represented by Formula 3B-1 below; and R3 and R4 are each independently a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted dibenzofuranyl group, or a substituted or unsubstituted dibenzothiophenyl group, a group represented by Formula 3A-1 below, or a group represented by Formula 3B-1 below:

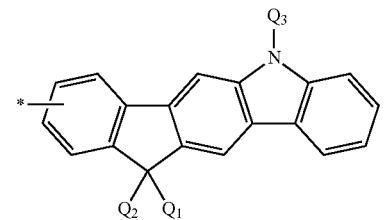

Formula 3A-1

Formula 3B-1

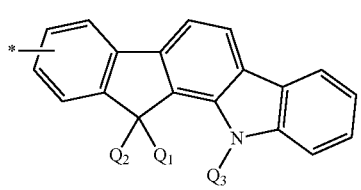

$Q_1$ to $Q_3$ are each independently a hydrogen atom, a heavy hydrogen atom, a halogen atom, a hydroxyl group, a cyano group, a nitro group, a carboxyl group, a $C_1$-$C_{10}$ alkyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted dibenzofuranyl group, or a substituted or unsubstituted dibenzothiophenyl group.

9. The condensed-cyclic compound of claim 1, wherein $R_1$ and $R_2$ are each independently a hydrogen atom, a heavy hydrogen atom, —F, a hydroxyl group, a cyano group, a nitro group, a carboxyl group, a substituted or unsubstituted $C_1$-$C_{10}$ alkyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted carbazolyl group, a substituted or unsubstituted benzoimidazolyl group, a substituted or unsubstituted triazinyl group, a substituted or unsubstituted dibenzopuranyl group, a substituted or unsubstituted dibenzothiophenyl group, a substituted or unsubstituted oxadiazolyl group, or a substituted or unsubstituted imidazopyridinyl group; and $R_3$ and $R_4$ are each independently a substituted or unsubstituted phenyl group, a substituted or unsubstituted naphthyl group, a substituted or unsubstituted fluorenyl group, a substituted or unsubstituted spirofluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted carbazolyl group, a substituted or unsubstituted benzoimidazolyl group, a substituted or unsubstituted triazinyl group, a substituted or unsubstituted dibenzopuranyl group, a substituted or unsubstituted dibenzothiophenyl group, a substituted or unsubstituted oxadiazolyl group, or a substituted or unsubstituted imidazopyridinyl group.

10. The condensed-cyclic compound of claim 1, wherein $R_3$ and $R_4$ are each independently selected from the group of compounds represented by Formulae 7A to 7O below:

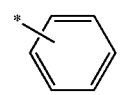

7A

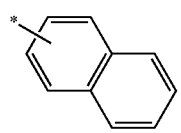

7B

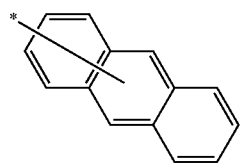

7C

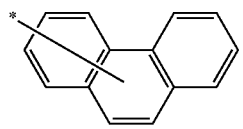

7D

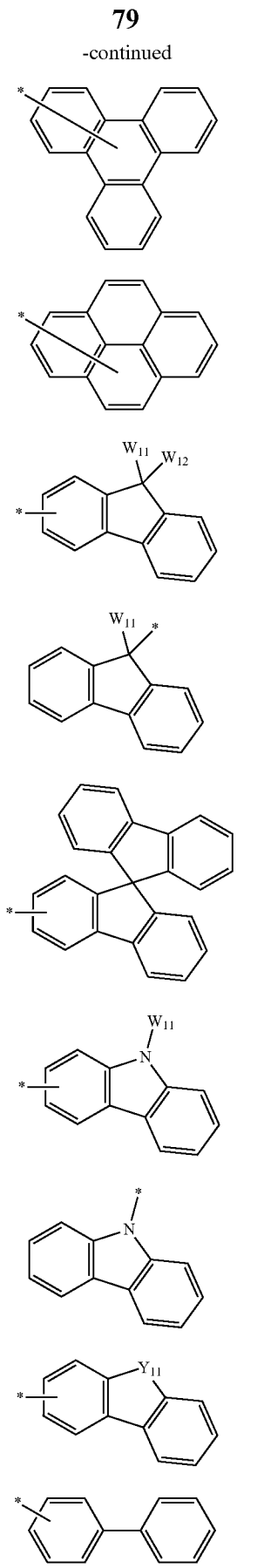

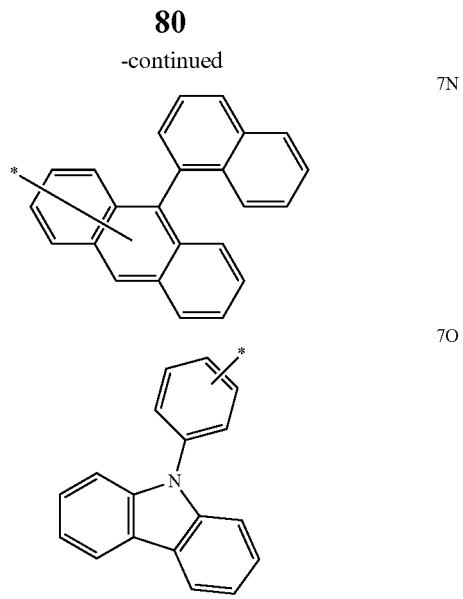

$Y_{11}$ is O or S; and $W_{11}$ and $W_{12}$ are each independently a hydrogen atom, a heavy hydrogen atom, a methyl group, an ethyl group, a propyl group, a butyl group, a pentyl group, a phenyl group, a naphthyl group, an anthryl group, or a carbazolyl group.

11. An organic light-emitting diode (OLED) comprising a first electrode, a second electrode disposed opposite to the first electrode; and a first layer interposed between the first electrode and the second electrode, wherein the first layer comprises a condensed-cyclic compound according to claim 1.

12. The OLED of claim 11, further comprising at least one layer selected from the group consisting of a hole injection layer, a hole transport layer, an emission layer, a hole blocking layer, an electron transport layer and an electron injection layer,
interposed between the first electrode and the second electrode in addition to the first layer.

13. The OLED of claim 12, wherein at least one layer is formed by a wet process.

14. The OLED of claim 11, wherein the first layer is a hole injection layer, a hole transport layer, or a single layer having both hole injecting and hole transporting capabilities.

15. The OLED of claim 11, wherein the first layer is an electron transport layer, an electron injection layer, or a single layer having both electron injecting and electron transporting capabilities.

16. The OLED of claim 11, wherein the first layer is an emission layer, and the condensed-cyclic compound is used as a fluorescent or phosphorescent host, wherein the first layer further comprises a fluorescent or phosphorescent dopant.

17. The OLED of claim 11, wherein the first layer is an emission layer, and the condensed-cyclic compound is used as a fluorescent dopant, wherein the first layer further comprises a fluorescent host or a phosphorescent host.

18. The OLED of claim 11, wherein the first layer is an emission layer, a hole transport layer, or an electron transport layer, wherein the first layer further comprises one or more compounds selected from the group consisting of anthracene-based, arylamine-based and styryl-based compounds.

19. The OLED of claim 11, wherein the first layer is a hole transport layer or an electron transport layer, wherein an emission layer is further interposed between the first electrode and the second electrode, wherein the emission layer comprises at least one region selected from the group consisting of a red emission region, a green emission region, a blue emission region and a white emission region, wherein at least one region of the red emission region, the green emission region, the blue emission region or the white emission region comprises a phosphorescent compound.

20. A flat panel display device comprising a transistor that comprises a source, a drain, a gate, and an active layer and the OLED diode of claim 11, wherein one of the source and the drain is electrically connected to the first electrode of the OLED.

21. The condensed-cyclic compound of claim 1, which is any one of Compounds 31 to 38 and 51 and 65:

31

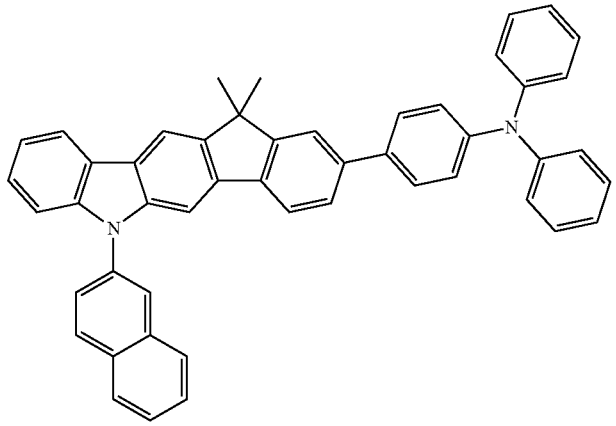

32

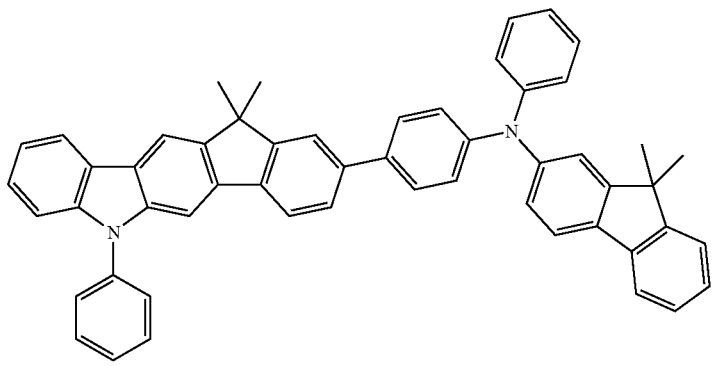

33

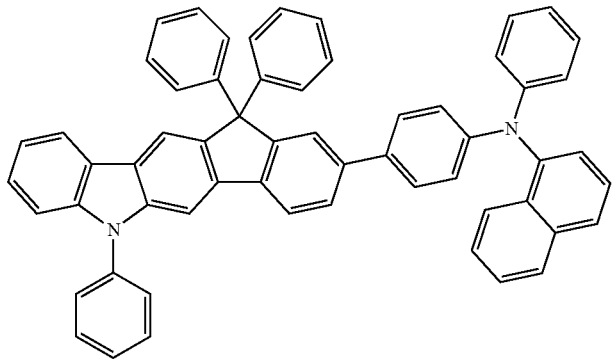

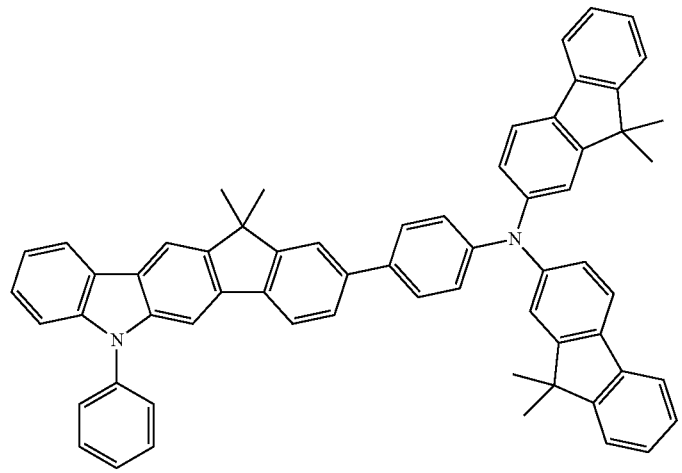
34
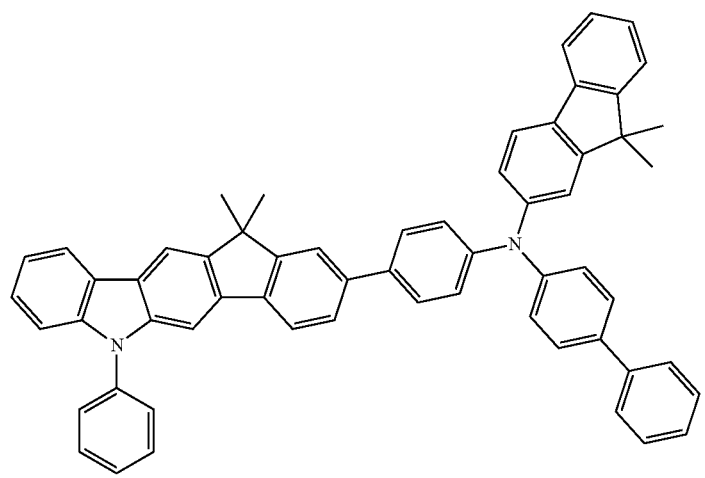
35
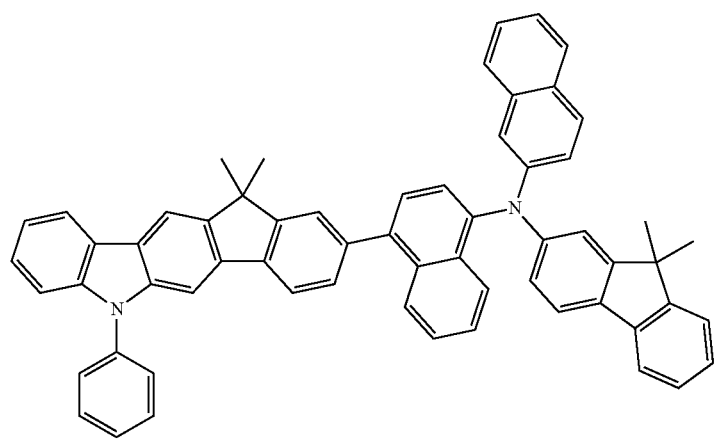
36

37
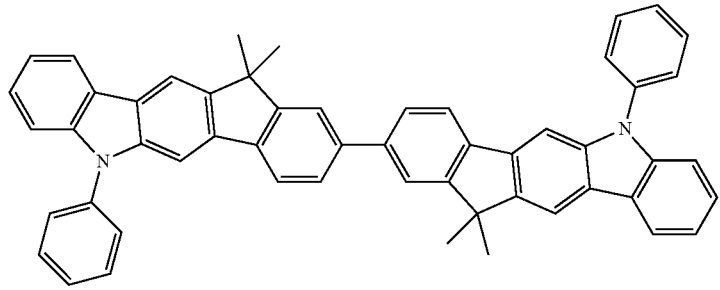
38
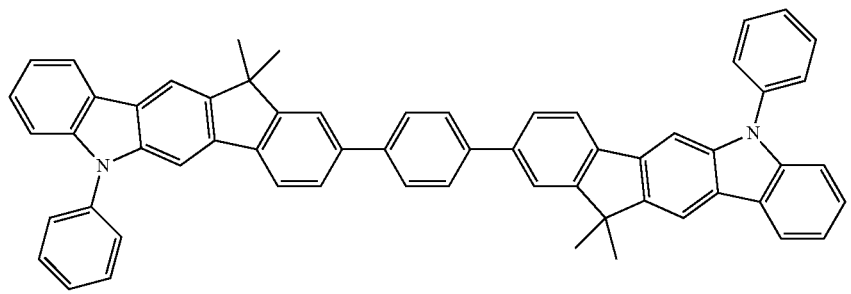
51
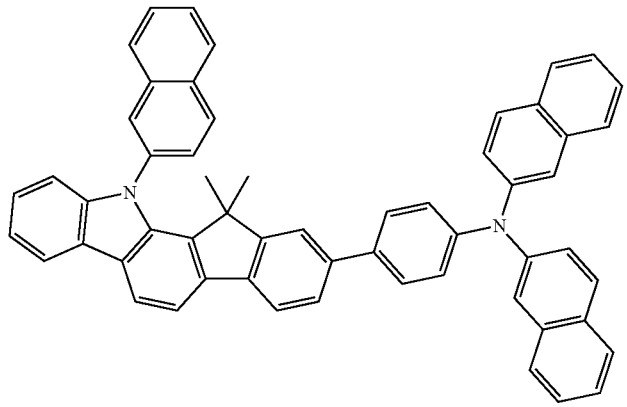
52
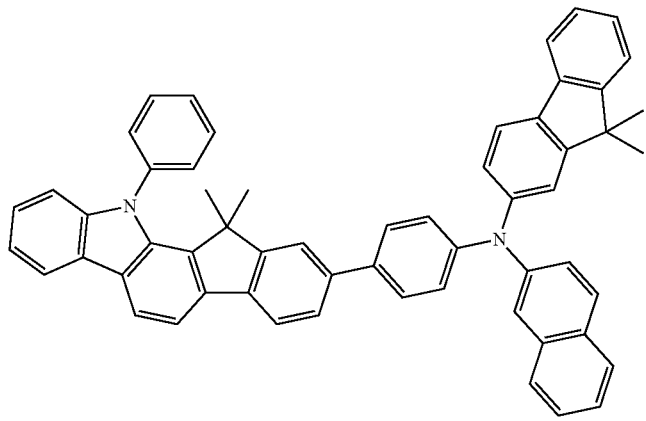

53
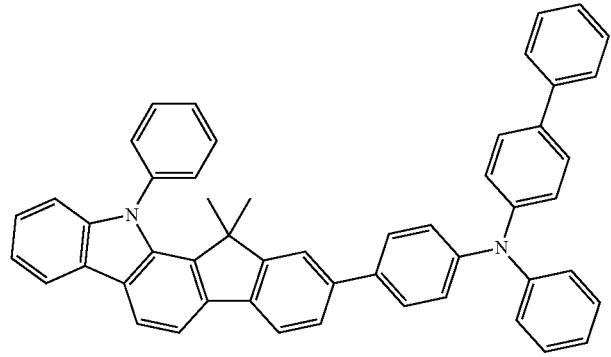
54
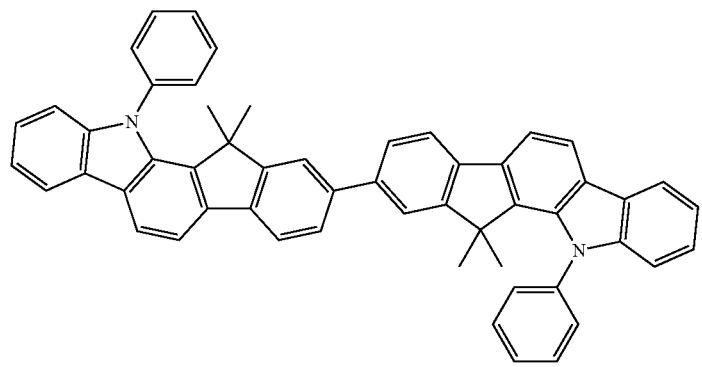
55
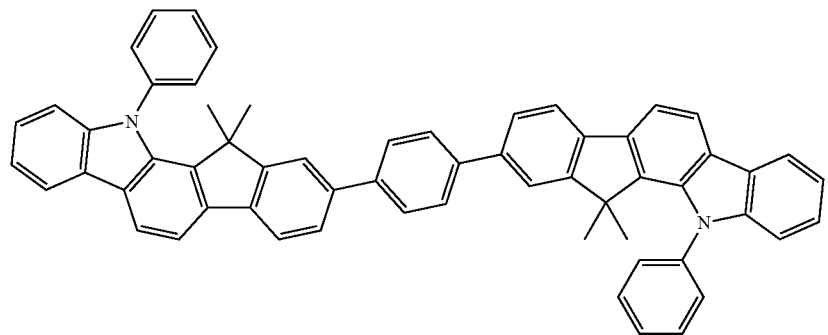
56
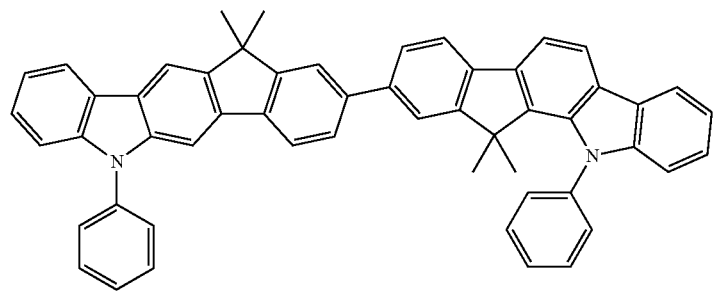

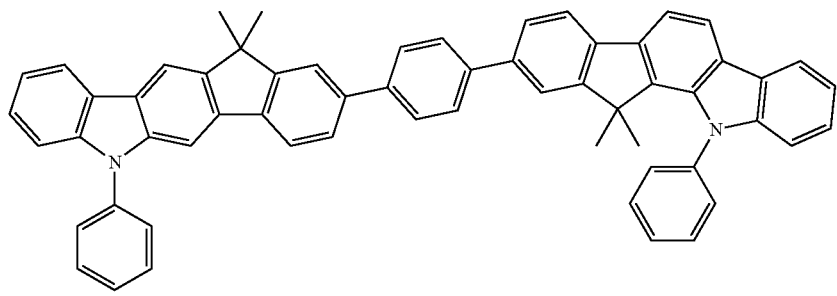
57
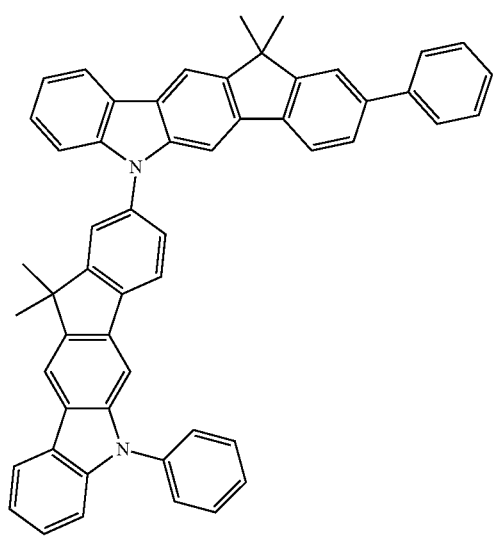
58
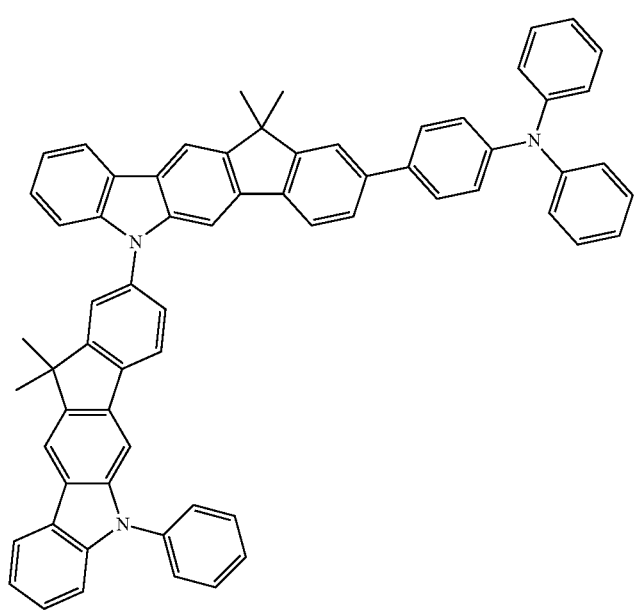
59

-continued
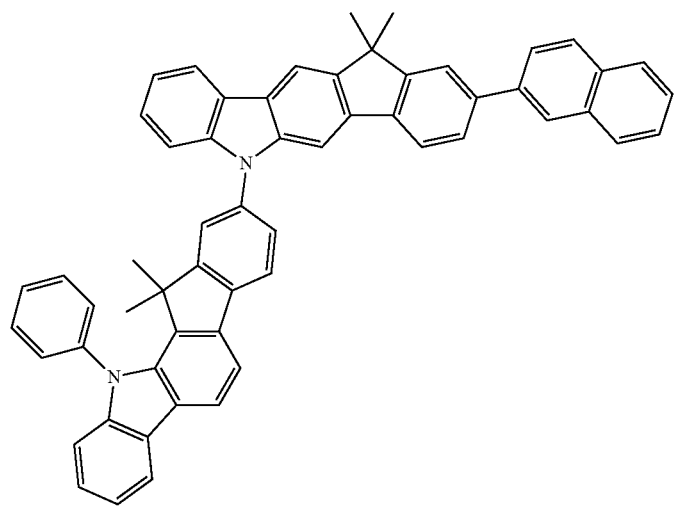
60
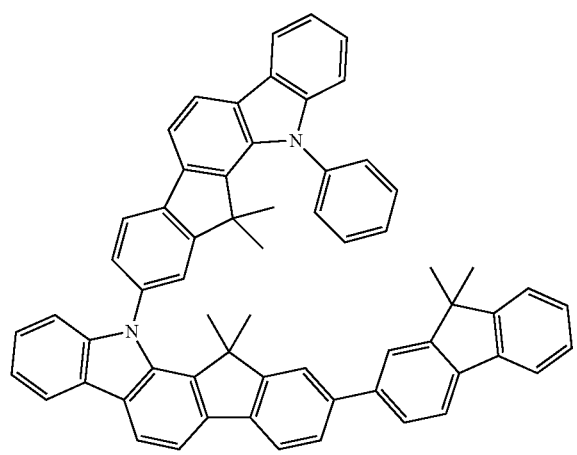
61
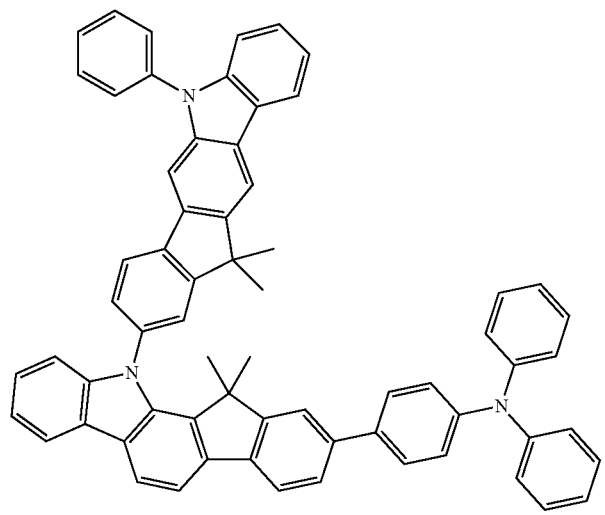
62